US007079956B2

(12) United States Patent
Ramakrishnan et al.

(10) Patent No.: US 7,079,956 B2
(45) Date of Patent: Jul. 18, 2006

(54) CRYSTAL STRUCTURE OF ANTIBIOTICS BOUND TO THE 30S RIBOSOME AND ITS USE

(75) Inventors: Venkatraman Ramakrishnan, Cambridge (GB); Ditlev Egeskov Brodersen, Cambridge (GB); Andrew Philip Carter, Cambridge (GB)

(73) Assignee: Medical Research Council, London (GB)

( * ) Notice: Subject to any disclaimer, the term of this patent is extended or adjusted under 35 U.S.C. 154(b) by 491 days.

(21) Appl. No.: 09/953,814

(22) Filed: Sep. 17, 2001

(65) Prior Publication Data

US 2004/0034207 A1    Feb. 19, 2004

Related U.S. Application Data

(63) Continuation-in-part of application No. 09/905,212, filed on Jul. 13, 2001.

(30) Foreign Application Priority Data

| Jul. 14, 2000 | (GB) | ................................. | 0017376.5 |
| Sep. 19, 2000 | (GB) | ................................. | 0022943.5 |
| Dec. 7, 2000 | (GB) | ................................. | 0029870.3 |
| Dec. 7, 2000 | (GB) | ................................. | 0029871.1 |
| Dec. 7, 2000 | (GB) | ................................. | 0029872.9 |
| May 3, 2001 | (GB) | ................................. | 0110885.1 |

(51) Int. Cl.
*G06F 19/00* (2006.01)
*C12Q 1/00* (2006.01)
*G01N 33/48* (2006.01)
*G01N 31/00* (2006.01)
*G06G 7/48* (2006.01)

(52) U.S. Cl. .............................. 702/27; 435/4; 702/19; 702/22; 703/11

(58) Field of Classification Search .................. 702/27; 530/350; 435/7.1
See application file for complete search history.

(56) References Cited

OTHER PUBLICATIONS

Jan Drenth, Principles of Protein X-ray Crystallography, 1995, Springer-Verlag, p. 16.*
News Focus, Science, Nov. 1, 2002, vol. 298, pp. 948-950.*
Hermann et al., J. Med. Chem., vol. 42, pp. 1250-1261, 1999.*
Purohit et al., Nature, vol. 370, pp. 659-662, 1994.*
Lorber et al., Protein Science, vol. 7, pp. 938-950, 1998.*
Voet et al., Biochemistry, John Wiley & Sons, Inc., p. 931, 1990.*
Allard, P. et al. (2000). "Another Piece of the Ribosome: Solution Structure of S16 and Its Location in the 30S Subunit," *Structure* 8(8): 875-882.

Blundell, T.L. et al. (1976). *Protein Crystallography*. Academic Press: New York, NY., and Johnson, L.N., eds. pp. ix-xiv (Table of Contents Only).
Broderson, D.E. et al. (2000). The Structural Basis for the Action of the Antibiotics Tetracycline, Pactamycin and Hygromycin B on the 30S Ribosomal Subunit, *Cell* 103:1143-1154.
Carter, A.P. et al. (2000). "Functional Insights from the Structure of the 30S Ribosomal Subunit and its Interactions with Antibiotics," *Nature* 407:340-348.
Clemons, W.M. et al. (2001). "Crystal Structure of the 30S Ribosomal Subunit from Thermus Thermophilus: Purification, Crystallization and Structure Determination," *J. Mol. Biol.* 310:827-843.
Collaborative Computational Project 4 (1994). "The CCP4 Suite: Programs for Protein Crystallography," *Acta Cryst.* D50:760-763.
Davies, C. et al. (1998). The Crystal Structure of Ribosomal Protein S4 Reveals a Two-Domain Molecule with an Extensive RNA-Binding Surface: One Domain Shows Structural Homology to the ETS DNA-Binding Motif, *EMBO. J.* 17:4545-4558.
De la Fortelle, E. and Bricogne, G. (1997). "Maximum-Likelihood Heavy-Atom Parameter Refinement for Multiple Isomorphous Replacement and Multiwavelength Anomalous Diffraction Methods," In *Methods in Enzymology*, Carter, C.W., Jr. Sweet, R.M., eds. Academic Press, New York, 1997, vol. 276 pp. 472-494.
Dunbrack, R.L. et al (1997). "Meeting Review: the Second Meeting on the Critical Assessment of Techniques for Protein Structure Prediction (CASP2), Asilomar, California, Dec. 13-16, 1996," *Folding and Design* 2(2): R27-R42.
Gabashvili, I.S. et al. (1999). "Major Rearrangements in the 70S Ribosomal 3D Structure Caused by a Conformational Switch in 16S Ribosomal RNA," *EMBO J.* 18(22): 6501-6507.

(Continued)

*Primary Examiner*—John S. Brusca
*Assistant Examiner*—Eric S. DeJong
(74) *Attorney, Agent, or Firm*—Ivor R. Elrifi; Mintz, Levin, Cohn, Ferris, Glovsky and Popeo, P.C.; Anthony D. Sabatelli

(57) ABSTRACT

The invention provides high resolution X-ray crystal structures of the 30S ribosome, obtained from *Thermus thermophilus* 30S subunit, having a tetragonal space group $P4_12_12$ to which are bound an antibiotic selected from the group paromomycin, streptomycin, spectinomycin, tetracycline, pactamycin and hygromycin B. An advantageous feature of the structure is that it diffracts at about 3 Å resolution. The invention also provides a crystal of 30S having the three dimensional atomic coordinates of the 30S ribosome, the coordinates being provided in any one of tables 1 to 4. The data may be used for the rational design and modelling of inhibitors for the 30S ribosome, which have potential use as antibiotics.

12 Claims, 7 Drawing Sheets

OTHER PUBLICATIONS

Golden, B.L. et al. (1993). "Ribosomal Protein S17 Characterization of the Three-Dimensional Structure by 1H- and 15N-NMR," *Biochemistry* 32:12812-12820.

Goodford, P.J. (1985). "A Computational Procedure for Determining Energetically Favorable Binding Sites on Biologically Important Macromolecules," *J.Med. Chem.* 28:849-857.

Greer, J. et al. (1994). "Application of the Three-Dimensional Structures of Protein Target Molecules in Structure-Based Drug Design," *J. of Medicinal Chemistry* 37:1035-1054.

Helgstrand, M. et al. (1999). "Solution Structure of the Ribosomal Protein S19 from Thermus Thermophius," *J. Mol. Biol.* 292:1071-1081.

Hope, H. et al. (1989). "Cryocrystallography of Ribosomal Particles," *Acta Cryst.* B45:190-199.

Hüttenhofer, A. and Noller, H.F. (1992). "Hydroxyl Radical Cleavage of tRNA in the Ribosomal P-Site," *Proc. Natl. Acad. Sci. USA* 89:7851-7855.

Jack, A. et al. (1976). "Crystallographic Refinement of Yeast Phenylalanine Transfer RNA at 2-5Å Resolution," *J.Mol. Biol* 108:619-649.

Markus, M.A. et al. (1998). "The Solution Structure of Ribosomal Protein S4 Delta41 Reveals Two Subdomains and a Positively Charged Surface that May Interact with RNA," *EMBO J.* 17(16):4559-4571.

Moazed, F. and Noller, H.F. (1987). "Interaction of Antibiotics with Functional Sites in 16S Ribosomal RNA," *Nature* 327:389-394.

Mougel, M. et al. (1993). "Minimal 16S rRNA Binding Site and Role of Conserved Nucleotides in *Escherichia coli* Ribosomal Protein S8 Recognition," *Eur. J. Biochem.* 215:787-792.

Mueller, F. and Brimacombe, R. (1997). "A New Model for the Three-Dimensional Folding of *Escherichia coli* 16 S Rimbosomal RNA. I. Fitting the RNA to a 3D Electron Microscopic Map at 20Å," *J. Mol. Biol.* 271:524-544.

Nowotny, V. and Nierhaus, K.H. (1988). "Assembly of the 30S Subunit from *Escherichia coli* Ribosomes Occurs via Two Assembly Domains which Are Initiated by S4 and S7," *Biochemistry* 27:7051-7055.

Ogle, M. et al. (2001). "Recognition of Cognate Transfer RNA by the 30S Ribosomal Subunit," *Science* 292:897-902.

Pioletti, M. et al. (2001). "Crystal Structures of Complexes of the Small Ribosomal Subunit with Tetracycline, Edeine and IF3," *EMBO Journal* 20(8): 1829-1839.

Prince, J.B. et al. (1982). "Covalent Crosslinking of tRNA 1Val to 16S RNA at the Ribosomal P-Site: Identification of Crosslinked Residues," *Proc. Natl. Acad. Sci. USA* 79:5450-5454.

Rich, A. and RajBhandary, U.L. (1976). "Transfer RNA: Molecular Structure, Sequence, and Properties," *In Annual Reviews of Biochemistry.* E.E. Snell et al., eds. Annual Reviews, Inc. Palo Alto, CA. pp. 805-860.

Rose, S.J. III et al. (1983). "Binding of Yeast tRNAPhe Anticodon Arm to *Escherichia coli* 30S Ribosomes," *J. Mol. Biol.* 167:103-117.

Schluenzen, F. et al. (2000). "Structure of Functionally Activated Small Ribosomal Subunit at 3.3 Å Resolution," *Cell* 102:615-623.

Tanaka, I. et al. (1998). "Matching the Crystallographic Structure of Ribosomal Protein S7 to a Three-Dimensional Model of the 16S Ribosomal RNA," *RNA* 4:542-550.

Urlaub, H. et al. (1997). "Identification and Sequence Analysis of Contact Sites Between Ribosomal Proteins and rRNA in *Escherichia coli* 30S Subunits by a New Approach Using Matrix-Assisted Laser Desorption/Ionaization-Mass Spectrometry Combined with N-Terminal Microsequencing," *J. Biol. Chem.* 272:14547-14555.

VanLoock, M.S. et al. (1999). "Major Groove Binding of the tRNA/mRNA Complex to the 16S Ribosomal RNA Decoding Site," *J. Mol. Biol.* 285:2069-2078.

von Ahsen, U. and Noller, H.F. (1995). "Identification of Bases in 16S rRNA Essential for tRNA Binding at the 30S Ribosomal P-Site," *Science* 267:234-237.

Walters, W.P. et al. (1998). "Virtual Screening—An Overview," *Drug Delivery Today* 3(4):160-178.

Wu, H. et al (1994). "The Binding Site for Ribosomal Protein S8 in 16S rRNA and spc mRNA from *Escherichia coli*: Minimum Structural Requirements and the Effects of Single Bulged Bases on S8-RNA Interaction," *Nucleic Acids Res.* 22(9):1687-1695.

* cited by examiner

Paromomycin

Spectinomycin

Primary tetracycline

Secondary tetracycline

Pactamycin

Hygromycin B

CRYSTAL STRUCTURE OF ANTIBIOTICS BOUND TO THE 30S RIBOSOME AND ITS USE

CROSS REFERENCE TO RELATED APPLICATIONS

This application claims priority from United Kingdom (U.K.) applications 0017376.5 filed Jul. 14, 2000, and 0022943.5 filed Sep. 19, 2000, 0029872.9 filed Dec. 7, 2000, 0029870.3 filed Dec. 7, 2000, 0029871.1 filed Dec. 7, 2000, and 01 10885.1 filed May 3, 2001, the contents of which are incorporated herein by reference. This application is a continuation-in-part of U.S. Ser. No. 09/905,212, filed Jul. 13, 2001.

This invention was made in part with U.S. Government support under NIH grant GM 44973 awarded by the PHS. The U.S. Government has certain rights in the invention.

FIELD OF THE INVENTION

The present invention relates to the provision of a high resolution crystal structure of the prokaryotic 30S ribosome subunit, particularly the 30S ribosome subunit bound to various antibiotics, and the use of this structure in drug discovery.

BACKGROUND OF THE INVENTION

The wealth of information made available through efforts in structural genomics and advances in computation has allowed structure-based drug design to emerge as a valuable tool in medicinal chemistry. In the past combinatorial chemistry, coupled with high-throughput approaches, shifted attention away from the more structure-based methods. Large-scale determination of protein structures is reversing the drug discovery process by starting with the protein structure and using it to identify and design new ligands. It is the integration of structure-based methods, virtual screening, and combinatorial chemistry that will provide the basis for more efficient drug design in the future, significantly reducing the time of the design cycle and the cost per marketed drug. Significant advances have already been made in AIDS, arthritis and cancer and in the treatment of hypertension (e.g. captopril).

Translation of the genetic code occurs on the ribosome, a large nucleoprotein complex that consists of two subunits. In bacteria, the two subunits are denoted 30S and 50S. The 50S subunit contains the catalytic site of peptidyl transferase activity, while the 30S subunit plays a crucial role in decoding messenger RNA. Protein synthesis is a complex, multistep process that requires several extrinsic GTP-hydrolysing protein factors during each of the main stages of initiation, elongation and termination. Despite several decades of work, the molecular details of the process are poorly understood, and the elucidation of the mechanism of translation is one of the fundamental problems in molecular biology today. A recent collection of articles summarizes the state of understanding of the field [1].

A contribution to this problem was made by Yonath and co-workers, who after nearly a decade of work showed that structures as large as the 50S ribosomal subunit would form crystals that diffract beyond 3 Å resolution [2]. The 30S ribosomal subunit (hereafter referred to as 30S) from *Thermus thermophilus* was originally crystallized by Trakhanov et al. in 2-methyl-2,4-pentanediol (MPD) [3] and soon afterwards by Yonath and co-workers in a mixture of ethyl-butanol and ethanol [4]. Subsequent work by both groups showed that the MPD crystal form diffracted to about 9–12 Å resolution [5, 6]. The diffraction limit of these crystals did not improve beyond 7 Å resolution for almost a decade, but more recently both Yonath and co-workers [7, 8] and Clemens et al. [9] obtained crystals of the MPD form that exhibit significantly improved diffraction. However, unlike the crystals obtained by the Yonath group [6], crystals, prepared according to the invention, do not require soaking in tungsten clusters or heat treatment in order to obtain high resolution diffraction.

The structure of the 30S at 5.5 Å resolution [9] has been described previously. All seven proteins whose structures were known at the time were placed in an electron density map. The structure of protein S20 was inferred to be a three-helix bundle, the fold of an entire domain of 16S RNA was traced, and a long RNA helix at the interface that contains the decoding site of the 30S was identified. Proteins S5 and S7 were also placed in electron density maps of the 30S obtained by Yonath and co-workers.

The 30S ribosomal subunit is a major target for antibiotics. The ribosome is a useful target for antibiotics since the structure of the 30S is widely conserved between prokaryotes, allowing for broad spectrum antibiotics. However, resistance to current antibiotics is currently a major problem in the field of medicine. There are presently very few new antibiotics available which can be used to treat the highly resistant strains of bacteria such as MRSA (methicilin resistant *Staphylococcus aureus*) which are becoming increasingly widespread.

Antibiotics act by interfering with various aspects of ribosome function. A detailed knowledge of antibiotic interactions with the ribosome could aid the development of new drugs against increasingly resistant strains of bacteria. 30S crystal structures described in the prior art are of relatively low resolution (greater than 3 Å). There is thus a need for a high resolution structure which can be useful in the development of novel therapeutics.

All references cited herein, including published patent applications and publications, are incorporated by reference in their entirety.

SUMMARY OF THE INVENTION

The invention is based upon determination of the structure of the 30S ribosomal subunit bound to a number of antibiotics at 3 Å resolution. The structure contains all of the ordered regions of 16S RNA and 20 associated proteins, and contains over 99% of the RNA sequence and 95% of the protein sequences, with the missing parts being exclusively at the termini of RNA or polypeptide chains.

The refined atomic resolution models of the 30S presented here allows the interpretation of a vast amount of biochemical data on its function in precise structural terms. The structure will also serve as a basis for the interpretation in molecular terms of lower resolution models of various functional states by electron-microscopy or X-ray crystallography. The 30S structure will help produce testable models for various aspects of ribosome function.

The invention provides for a crystal of a 30S ribosomal subunit bound to an antibiotic selected from the group consisting of paromomycin, streptomycin, spectinomycin, tetracycline, pactamycin and hygromycin B, the crystal having a resolution of less than 3 Å.

The invention provides for a crystal of 30S having the three dimensional atomic coordinates of Table n, where Table n is any one of Tables 1 to 4. The binding of the antibiotics paromomycin, spectinomycin and streptomycin are shown in the coordinates of Table 1A. More refined coordinates are shown in Table 1B. Thus, in some embodiments, reference herein to "Table 1" is a reference to either of Table 1A or 1B (or where the context permits, both; i.e., reference to "Table 1" can refer to Table 1A and/or Table 1B). Further, Table 1C represents a further data set for the antibiotic paromomycin bound to the 30S ribosome, and thus where the antibiotic Z is paromomycin, reference to Table 1 (or Table n where 1 is included) means any one of 1A, 1B or 1C or any combination of Tables 1A, 1B, and/or 1C, i.e., Table 1A and/or Table 1B and/or Table 1C, preferably Table 1A or Table 1B or Table 1C.

Thus, for example, where it is stated that the invention refers to computer readable media with "atomic coordinate data according to Table 1 recorded thereon", this means that the media has either the data of Table 1A, or the data of Table 1B (and in the case of paromomycin, or Table 1C) or both (or in the case of paromomycin, any two or all three of the tables), recorded thereon. Likewise, reference to Table n where n is 1, also means either or both of 1A and/or 1B (and in the case of paromomycin, and/or 1C).

Equally, it will be understood that Table 1A or Table 1B may be provided with the data derived from the 30S ribosome with only a single antibiotic data set provided, and such a table forms a part of the invention.

Table 1 provides the coordinates of the 30S ribosome bound to the antibiotics paromomycin, spectinomycin and streptomycin (1A and 1B), and paromomycin alone (1C), as described above. Table 2 provides the coordinates of the 30S ribosome bound to tetracycline (primary and secondary sites). Table 3 provides the coordinates of the 30S ribosome bound to pactamycin. Table 4 provides the coordinates of the 30S ribosome bound to hygromycin B.

The invention also provides for a crystal of a 30S ribosomal subunit bound to an antibiotic having the structure defined by the co-ordinates of a table selected from the group of tables 1 to 4.

In one embodiment, the crystal structure is formed by a method that does not use heavy atom clusters or heat activation.

In another embodiment, the 16S RNA of the 30S subunit comprises the 885–888/910–912 base pairing conformation.

The invention also provides for a crystal of a 30S subunit bound to an antibiotic Z, (wherein Z is one of the antibiotics defined below), having a tetragonal space group $P4_12_12$ with unit cell dimensions, for each of the antibiotics Z, of:

| Z | a (Angstroms) | b (Angstroms) | c (Angstroms) |
| --- | --- | --- | --- |
| Paromomycin | 401.375 | 401.375 | 175.887 |
| Paromomycin | 401.2 | 401.2 | 176.4 |
| Streptomycin | 401.375 | 401.375 | 175.887 |
| Spectinomycin | 401.375 | 401.375 | 175.887 |
| Tetracycline | 401.158 | 401.158 | 176.944 |
| Pactamycin | 401.719 | 401.719 | 177.002 |
| Hygromycin B | 402.063 | 402.063 | 175.263 |

The invention also provides for a crystal of a 30S subunit bound to the antibiotic paromomycin having a tetragonal space group $P4_12_12$ with unit cell dimensions of a=401.4 Å, b=401.4 Å, c=175.9 Å.

The invention also provides for a crystal of a 30S subunit bound to the antibiotic paromomycin having a tetragonal space group $P4_12_12$ with unit cell dimensions of a=402.0 Å, b=402.0 Å, c=176.5 Å.

The invention also provides for a crystal of a 30S subunit bound to the antibiotic paromomycin having a tetragonal space group $P4_12_12$ with unit cell dimensions of a=401.2 Å, b=401.2 Å, c=176.4 Å.

The invention also provides for a crystal of a 30S subunit bound to the antibiotic Streptomycin having a tetragonal space group $P4_12_12$ with unit cell dimensions of a=401.4 Å, b=401.4 Å, c=175.9 Å.

The invention also provides for a crystal of a 30S subunit bound to the antibiotic Streptomycin having a tetragonal space group $P4_12_12$ with unit cell dimensions of a=402.0 Å, b=402.0 Å, c=176.5 Å.

The invention also provides for a crystal of a 30S subunit bound to the antibiotic Spectinomycin having a tetragonal space group $P4_12_12$ with unit cell dimensions of a=401.4 Å, b=401.4 Å, c=175.9 Å.

The invention also provides for a crystal of a 30S subunit bound to the antibiotic Spectinomycin having a tetragonal space group $P4_12_12$ with unit cell dimensions of a=402.0 Å, b=402.0 Å, c=176.5 Å.

The invention also provides for a crystal of a 30S subunit bound to the antibiotic Tetracycline having a tetragonal space group $P4_12_12$ with unit cell dimensions of a=401.2 Å, b=401.2 Å, c=176.9 Å.

The invention also provides for a crystal of a 30S subunit bound to the antibiotic Pactamycin having a tetragonal space group $P4_12_12$ with unit cell dimensions of a=401.7 Å, b=401.7 Å, c=177.0 Å.

The invention also provides for a crystal of a 30S subunit bound to the antibiotic Hygromycin B having a tetragonal space group $P4_12_12$ with unit cell dimensions of a=402.1 Å, b=402.1 Å, c=175.3 Å.

The invention also provides for a computer-based method of rational drug design which comprises: a) providing the structure of a 30S ribosomal subunit as defined by the coordinates of a table selected from the group of tables 1 to 4; b) providing the structure of a candidate modulator molecule; c) fitting the structure of the candidate to the structure of the 30S of the table to provide a result; and d) comparing the result with a structure comprising the 30S ribosome of the table in combination with at least one antibiotic structure of the table, wherein the antibiotic is selected from the group consisting of paromycin, streptomycin, spectinomycin, tetracycline, pactamycin and hygromycin.

The invention also provides for a computer-based method of rational drug design which comprises: a) providing the structure of a 16S RNA of the 30S ribosome as defined by the coordinates of a table selected from the group of tables 1 to 4; b) providing the structure of a candidate modulator molecule; c) fitting the structure of the candidate to the structure of the 16S RNA of the 30S ribosome of the table to provide a result; and d) comparing the result with a structure comprising the 16S RNA of the 30S ribosome of the table in combination with at least one antibiotic structure of the table, wherein the antibiotic is selected from the group consisting of paromycin, streptomycin, spectinomycin, tetracycline, pactamycin and hygromycin.

The invention also provides for a computer-based method of rational drug design which comprises: a) providing the coordinates of at least one atom of the 30S ribosome as presented in a table selected from the group of tables 1 to 4; b) providing the structure of a candidate modulator molecule; c) fitting the structure of the candidate to the coordinates of the 30S of the table to provide a result; and d) comparing the result with a structure comprising the coordinates of the 30S ribosome of the table in combination with at least one antibiotic structure of the table, wherein the antibiotic is selected from the group consisting of paromycin, streptomycin, spectinomycin, tetracycline, pactamycin and hygromycin.

In one embodiment of this method the coordinates comprise a subdomain of the 30S ribosome.

In another embodiment of this method, the coordinates are selected from at least one member of any one of the following groups of residues:
Group I: G1405, A1408, C1490, G1491, A1493, G1494 and U1495;
Group II: G1064, C1066, G1068 and C1192;
Group III: U14, C526, G527, A913, A914, C1490, G1941 and S12Lys45;
Group IV: A965, G966, G1053, C1054, C1195, U1196, G1197 and G1198;
Group V: U244, A892 and C893;
Group VI: G693, A694, C788, C795, C796, S7Gly81, and optionally U1540; and
Group VII: C1403, G1405, G1494, U1495, C1496 and U1498.

The invention also provides for a computer-based method of rational drug design which comprises: a) providing the coordinates of at least a sub-domain of the 30S ribosome as defined by the coordinates presented in a table selected from the group of tables 1 to 4; b) providing the structure of a candidate modulator molecule; c) fitting the structure of the candidate to the coordinates of the 30S of the table to provide a result; and d) comparing the result with a structure comprising the coordinates of the 30S ribosome sub-domain of the table in combination with at least one antibiotic structure of the table, wherein the antibiotic is selected from the group consisting of paromycin, streptomycin, spectinomycin, tetracycline, pactamycin and hygromycin.

The invention also provides for a computer-based method for identifying a potential inhibitor of the 30S ribosome comprising the steps of: a) employing a three-dimensional structure of 30S, or at least one sub-domain thereof, to characterise at least one active site, the three-dimensional structure being defined by atomic coordinate data according to a table selected from the group of tables 1 to 4; and b) identifying the potential inhibitor by designing or selecting a compound for interaction with the active site.

In one embodiment, this method further comprises the steps of: c) obtaining or synthesizing the potential inhibitor; and d) contacting the potential inhibitor with 30S to determine the ability of the inhibitor to interact with the 30S.

In another embodiment, this method further comprises the steps of: c) obtaining or synthesising the potential ligand; d) forming a complex of 30S and the potential ligand; and e) analysing the complex by X-ray crystallography to determine the ability of the potential ligand to interact with 30S.

In another embodiment, the 30S ribosome is derived from a bacterial source that is not *T. thermophilus*.

The invention also provides for a computer system, intended to generate structures and/or perform rational drug design for the 30S ribosome or complexes of the 30S ribosome with a potential modulator, the system containing either (a) atomic coordinate data according to a table selected from the group of tables 1 to 4, the data defining the three-dimensional structure of 30S or at least one sub-domain thereof, or (b) structure factor data for 30S, the structure factor data being derivable from the atomic coordinate data of a table selected from the group of tables 1 to 4.

The invention also provides for a computer readable media with either (a) atomic coordinate data according to a table selected from the group of tables 1 to 4 recorded thereon, the data defining the three-dimensional structure of the 30S ribosome, at least one atom or at least one subdomain thereof, or (b) structure factor data for the 30S ribosome recorded thereon, the structure factor data being derivable from the atomic coordinate data of a table selected from the group of tables 1 to 4.

The invention also provides for a method for modelling a structure of a 30S ribosome bound to an antibiotic selected from the group consisting of paromomycin, streptomycin, spectinomycin, tetracycline, pactamycin and hygromycin B comprising the steps of: a) providing an atomic model of a structure wherein the structure has a resolution of greater than 3 Å; b) comparing the structure obtained in a) with the data presented in Table 1; and c) refining the model to resolve the structure and provide higher resolution.

In one embodiment, the 30S ribosome is derived from a bacterial source that is not *T. thermophilus*.

30S crystals do not contain the S1 subunit protein. Selective removal of the S1 subunit prior to crystallization is shown to improve the resolution of the crystals of the 30S subunit according to the invention described herein. Although the atomic co-ordinates, provided herein, allow those of skill in the art to bypass the need to undertake the crystallization of the 30S, this crystallization method nonetheless forms a further aspect of the invention.

The invention also provides for a method for crystallizing the 30S subunit bound to an antibiotic selected from the group consisting of paromomycin, streptomycin, spectinomycin, tetracycline, pactamycin and hygromycin B, comprising the steps of: a) providing a 30S subunit; b) removing the S1 subunit therefrom; c) cocrystallizing the 30S subunit with the antibiotic or soaking the antibiotic into crystals of the 30S; and d) freezing the crystal.

The invention also provides for a method for crystallizing the 30S subunit bound to an antibiotic selected from the group consisting of paromomycin, streptomycin, spectinomycin, tetracycline, pactamycin and hygromycin B, comprising the steps of: a) providing a 30S subunit, b) cocrystallizing the 30S subunit with the antibiotic or soaking the antibiotic into crystals of the 30S; and c) freezing the crystal, wherein the crystallization is performed under conditions wherein crystals only form from a 30S subunit that lacks the S1 subunit.

The invention also provides for a method of identifying a binding partner of the 30S subunit comprising the steps of: a) characterizing an active site of the 30S subunit, wherein the active site is bound by an antibiotic, and b) designing or selecting a compound that interacts with the active site.

In one embodiment, the active site is characterized from the three-dimensional structure of the 30S subunit.

In another embodiment, the active site is characterized from the three-dimensional structure of at least one sub-domain of the 30S subunit.

In another embodiment, the binding partner is an inhibitor of the 30S subunit.

The invention also provides for a method of designing a molecule that interacts with an active site of the 30S subunit, wherein the active site is bound to an antibiotic, comprising analyzing the three dimensional structure of the 30S subunit by a computer modelling program.

The invention also provides for a method of preparing a computer fitting model of binding of a binding partner that binds to an active site of the 30S subunit and the 30S subunit, wherein the active site is bound to an antibiotic comprising analyzing the binding partner and the 30S subunit by a docking program selected from the group consisting of: GRAM, DOCK, AUTODOCK or GRID.

The invention also provides for a method of determining the activity of a binding partner of the 30S subunit wherein the binding partner binds to an active site of the 30S subunit that is bound by an antibiotic comprising the steps of: a) obtaining or synthesizing the binding partner; b) contacting the 30S subunit with the binding partner under conditions wherein the binding partner is active; and c) determining the activity of the 30S subunit.

The invention also provides for a method of characterizing the binding of a binding partner of the 30S subunit to the 30S subunit, wherein the binding partner binds to an active site of the 30S subunit that is bound by an antibiotic, comprising the steps of: comprising the steps of: a) obtaining or synthesizing the binding partner; b) contacting the 30S subunit with the binding partner; c) forming a complex of the 30S subunit and the binding partner; and d) analyzing the complex by X-ray crystallography.

In one embodiment, the binding partner is an inhibitor of the 30S subunit.

The invention also provides for a method of analyzing a 30S-ligand complex, wherein the ligand is an antibiotic selected from the group consisting of paromomycin, streptomycin, spectinomycin, tetracycline, pactamycin and hygromycin B, comprising the steps of: a) obtaining X-ray crystallographic diffraction data from the 30S-ligand complex; b) obtaining a three-dimensional structure of the 30S subunit or at least one subdomain of the 30S subunit; andc) using the data obtained in a) and b) to generate a difference Fourier electron density map of the complex.

In one embodiment, the three-dimensional structure is defined by atomic coordinate data presented in the group consisting of: Table 1, 2, or 3.

In another embodiment, the three dimensional structure is further defined by atomic coordinate data presented in Table 4 or 5.

The invention also provides for a method of modelling the structure of a mutant 30S subunit bound to an antibiotic selected from the group consisting of paromomycin, streptomycin, spectinomycin, tetracycline, pactamycin and hygromycin B, comprising the steps of: a) providing the structure of the 30S ribosome of Table 1, 2 or 3; b) changing at least one amino acid of the structure to provide the mutant 30S subunit; and c) modelling the structure of the 30S mutant.

The invention also provides for a method of modelling the structure of a mutant 30S subunit bound to an antibiotic selected from the group consisting of paromycin, streptomycin, spectinomycin, tetracycline, pactamycin and hygromycin B, comprising the steps of: a) providing the structure of the 30S ribosome of Table 1, 2 or 3; b) changing at least nucleotide of the structure to provide the mutant 30S subunit; and c) modelling the structure of the 30S mutant.

In one embodiment, step b) is repeated.

The invention also provides for a method of analyzing a 30S-ligand complex wherein the ligand is an antibiotic selected from the group consisting of paromycin, streptomycin, spectinomycin, tetracycline, pactamycin and hygromycin B comprising the steps of: a) cocrystallizing the 30S and the ligand or soaking the ligand into crystals of the 30S; b) collecting x-ray crystallographic data from the crystals of the 30S-ligand complex; c) using the three-dimensional structure of Table 1 or at least one sub-domain thereof, to generate a difference Fourier electron density map of the 30S-ligand; and d) modelling the ligand in the difference Fourier electron density map.

In one embodiment, the S1 subunit is removed from the 30S prior to the co-crystallization step.

In another embodiment, the co-crystallization is performed under conditions wherein crystals only form from a 30S subunit that lacks the S1 subunit.

DESCRIPTION OF TABLES ACCOMPANYING CD-ROM (37 C.F.R. §§1.52 & 1.58

Figure 1:
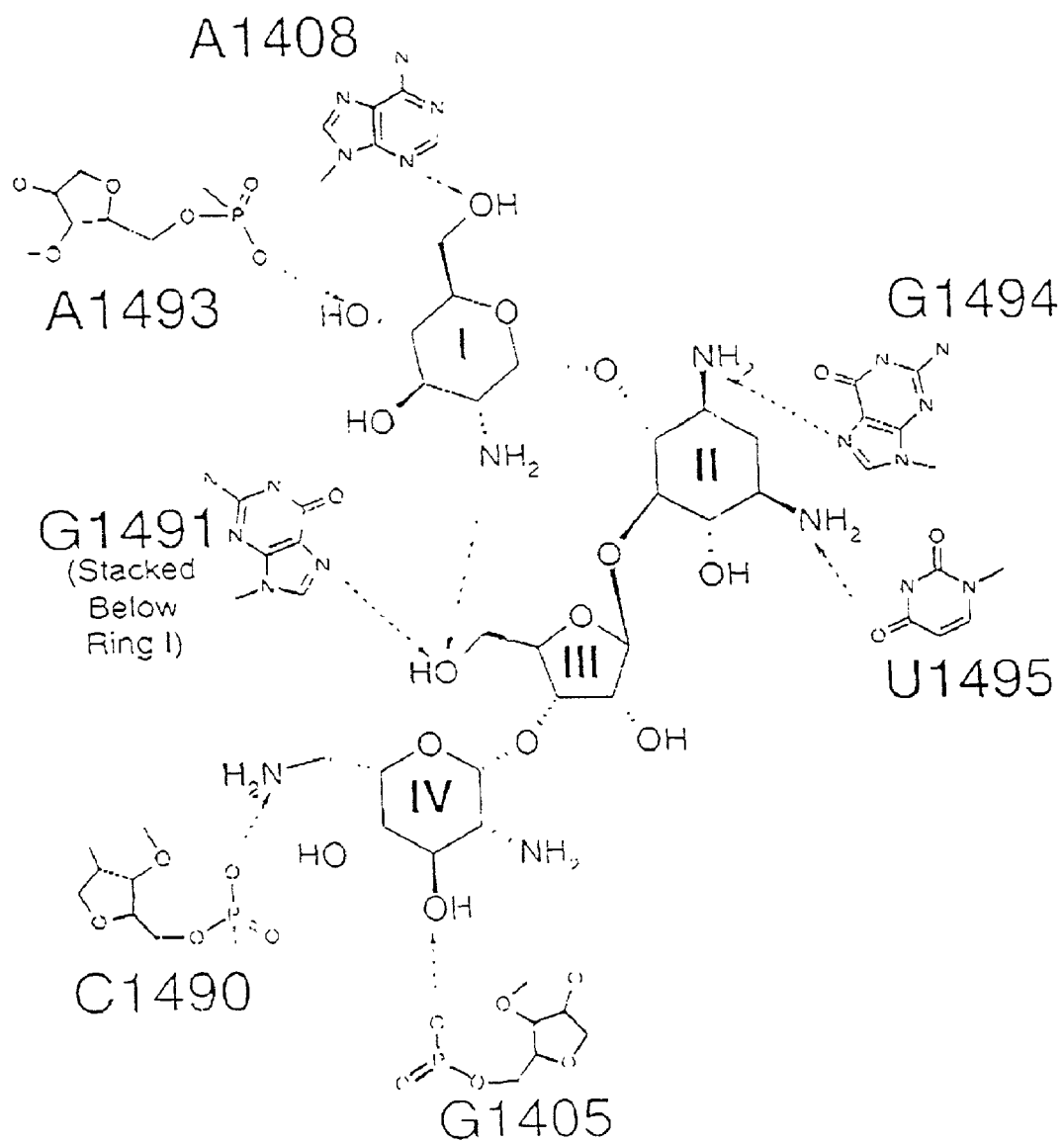
FIG. 1 shows the binding of paromomycin to the 30S ribosome.

Tables 1A, 1B, 1C, 2, 3 and 4 referred to herein are filed herewith on CD-ROM in accordance with 37 C.F.R. §§1.52 and 1.58. Two identical copies (marked "Copy 1" and "Copy 2") of the CD-ROM both of which contain Tables 1A, 1B, 1C, 2, 3 and 4, are submitted herewith, for a total of two CD-ROM discs submitted. The contents of all files contained on the CD-ROM discs submitted with this application are hereby incorporated by reference into the specification.

Table 1A is recorded as "Table 1A.txt" created Jul. 12, 2001, size 3,896 KB, and provides the coordinates of the 30S ribosome bound to the antibiotics paromomycin, spectinomycin and streptomycin.

Table 1B is recorded as "Table 1B.txt" created on Jul. 12, 2001, size 4,168 KB, and provides the coordinates of the 30S ribosome bound to the antibiotics paromomycin, spectinomycin and streptomycin.

Table 1C is recorded as "Table 1C.txt" created on Jul. 12, 2001, size 3,944 KB, and provides the coordinates of the 30S ribosome bound to the antibiotic paromomycin alone.

Table 2 is recorded as "Table 2.txt" created on Jul. 12, 2001, size 3,949 KB, and provides the coordinates of the 30S ribosome bound to tetracycline (primary and secondary sites).

Table 3 is recorded as "Table 3.txt" created on Jul. 12, 2001, size 3,947 KB, and provides the coordinates of the 30S ribosome bound to pactamycin.

Table 4 is recorded as "Table 4.txt" created on Jul. 12, 2001, size 3,947 KB, and provides the coordinates of the 30S ribosome bound to hygromycin B.

DETAILED DESCRIPTION OF THE INVENTION

The invention provides a high resolution crystal structure of the 30S ribosome subunit, in particular, in complex with an antibiotic, and the use of this structure for drug discovery.

Definitions.

"A", "an", "the" and the like, unless otherwise indicated include plural forms.

The term "sub-domain" includes any one or more of the following:
(a) an element selected from the following:
   at least one complete element of secondary structure, i.e. an alpha helix or a beta sheet, or RNA helix, as described in the detailed description below;
   a group of two or more such elements which interact with each other;
   at least one subunit protein;
   a subgroup of subunit proteins, for example a group which includes two or more proteins which are found to interact with each other;
   any of the above, when the protein(s) or element(s) thereof is used in conjunction with all or part of the 16S RNA structure associated with the element(s) or protein(s);
(b) a space of volume defining a region around any one particular atom of interest (e.g. an atom involved in binding to an antibiotic), the volume being less than the total volume of the tetragonal space of the complete crystal. For example, the coordinates of atoms in a volume of from about 500 to about 15,000 $Å^3$ may be selected and used for the present invention. Such a space may be a sphere having a diameter of from about 10 Å to about 30 Å, centred around a point of interest; and
(c) a collection of at least about 10, e.g. at least about 25 such as at least about 50, more preferably at least about 100, even more preferably at least about 500 atoms and most preferably at least about 1000 atoms defined by the coordinates of Table 1, wherein at least 2 of the atoms, and preferably at least about 50% of the atoms of the collection are located within about 50 Å of each other.

An "active site" of the 30S is any part of this structure involved in tRNA or mRNA binding, factor binding or translocation. This includes regions responsible for binding initiation factors, elongation factor G or release factors, regions which are target sites for regulation by co-factors, phosphorylation or acetylation, and regions responsible for interaction with the 50S ribosome. It also includes regions which change conformation during translocation or protein synthesis, particularly one or more of the 16S RNA helices 18, 27, 34 and 44.

Particular regions of the 30S include antibiotic binding regions. Other regions include the three tRNA binding sites, i.e. the aminoacyl (A), peptidyl (P) and exit (E) sites. Other active sites are those which undergo movement during translocation of tRNAs from the A to P sites and the P to E sites. Regions further include any one of the subunit proteins S2 to S20 and THX, including any of the individually identified subunit proteins in the accompanying examples.

By "fitting", is meant determining by automatic or semi-automatic means, interactions between one or more atoms of a potential inhibitor molecule and one or more atoms or binding sites of the 30S, and calculating the extent to which such interactions are stable. Various computer-based methods for fitting are described further herein.

The term "fit" refers to the result of "fitting" when comparison step shows identical or substantially the same coordinates to a 30S ribosomal subunit bound by one or more antibiotics including, but not limited to, paromomycin, streptomycin, spectinomycin, tetracycline, pactamycin or hygromycin B as defined herein The term "root mean square deviation" means the square root of the arithmetic mean of the squares of the deviations from the mean.

"Computer readable media" refers to any media which can be read and accessed directly by a computer. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

A "computer system" refers to the hardware means, software means and data storage means used to analyse the atomic coordinate data of the present invention. The minimum hardware means of the computer-based systems of the present invention comprises a central processing unit (CPU), input means, output means and data storage means. Desirably a monitor is provided to visualise structure data. The data storage means may be RAM or means for accessing computer readable media of the invention. Examples of such systems are laptops as well as microcomputer workstations available from Silicon Graphics Incorporated and Sun Microsystems running Unix based, Linux, Windows NT or IBM OS/2 operating systems.

A "ligand" is any chemical moiety (organic or inorganic) that binds or interacts, generally but not necessarily specifically, to or with another chemical entity.

The term "space group" refers to the arrangement of symmetry elements of a crystal. The International Union of Crystallographers has determined that there are 230 unique ways in which chemical substances, proteins or otherwise, may assemble in three-dimensions to form crystals. These are called the 230 "space groups." The designation of the space group in addition to the unit cell constants (which define the explicit size and shape of the cell, which repeats within the crystal) is routinely used to uniquely identify a crystalline substance.

A "tetragonal space group" refers to a crystal system characterized by three axes at right angles of which only the two lateral axes are equal.

The term "molecular replacement" refers to a method that involves generating a preliminary atomic model of a crystal, whose structure coordinates are unknown, by orienting and positioning a related crystal structure whose structure coordinates are known. Phases are calculated from this model and combined with the observed amplitudes to give an approximate Fourier synthesis of the structure whose coordinates are unknown. This, in turn, can be subject to any of the several forms of refinement, as defined herein, to provide a final, accurate structure of the unknown crystal. Lattman, E., "Use of the Rotation and Translation Functions," in *Methods in Enzymology*, 115, pp. 55–77 (1985); M. G. Rossmann, ed., "The Molecular Replacement Method", *Int. Sci. Rev.* Ser., No. 13, Gordon & Breach, New York, (1972). Using the structure coordinates of a 30S ribosomal subunit provided by this invention, molecular replacement may be used to determine the structure coordinates of a crystalline mutant or homologue of a 30S ribosomal subunit, or of a different crystal form of a 30S ribosomal subunit bound to a modulator compound.

As used herein, the term "modulator" compound refers to a compound that increases or decreases the activity of the 30S ribosomal subunit according to the invention. A candidate modulator may be said to inhibit or decrease activity if the translational activity of the associated intact ribosome is reduced, for example by more than 10%, (for example, 11%, 20%, 30%, 50%, 100% etc.) in the presence of modulator when compared to values obtained in the absence of modulator. A candidate modulator may be said to activate or increase activity if the translational activity of the associated intact ribosome is increased for example by more than 10%, (for example, 11%, 20%, 30%, 50%, 100% etc.) in the presence of the modulator when compared to values obtained in the absence of the modulator. A candidate modulator may also be said to activate or increase activity if the translational activity of the associated intact ribosome is increased for example by at least 2-fold, (for example 3, 5, 10, 100, 1000 or 10,000-fold or more) in the presence of the modulator when compared to values obtained in the absence of a modulator. A modulator can be a protein, a nucleic acid, or an antibody or fragment thereof, a peptide, an organic molecule etc. . . . Candidate modulators can be natural or synthetic compounds, including, for example, antibiotics and derivatives thereof.

As used herein, the term "forming a complex" refers to covalent or non-covalent association of the 30S subunit of the invention with a candidate modulator compound. A complex may also encompass accessory factors and/or inhibitors or activators associated with the 30S subunit according to the invention.

As used herein, an "interaction" refers to a condition of proximity between a chemical entity or compound, or portions thereof, with the 30S ribosomal subunit according to the invention. The association or interaction may be non-covalent—wherein the juxtaposition is energetically favored by hydrogen bonding or van der Waals or electrostatic interactions—or it may be covalent.

As used herein, "structure coordinates" refers to mathematical coordinates derived from mathematical equations related to the patterns obtained on diffraction of a monochromatic beam of X-rays by the atoms (scattering centers) of a 30S ribosomal subunit complex in crystal form. The diffraction data are used to calculate an electron density map of the repeating unit of the crystal. The electron density maps are then used to establish the positions of the individual atoms within the unit cell of the crystal.

The term "unit cell" refers to a basic parallelepiped shaped block. The entire volume of a crystal may be constructed by regular assembly of such blocks. Each unit cell comprises a complete representation of the unit of pattern, the repetition of which builds up the crystal. Using the structure coordinates of the 30S ribosomal subunit complex provided by this invention, molecular replacement may be used to determine the structure coordinates of a crystalline mutant or homologue of the 30S ribosomal subunit complex or of a different crystal form of the 30S ribosomal subunit bound by a candidate modulator compound such as an antibiotic or other small organic molecule.

In drug design, the binding site for a drug is usually defined by the location of the natural active site or the location of the recognition site for a natural ligand. It is normally found experimentally by studying a complex formed between the target molecule of interest, for example a protein or the 30S ribosomal subunit, with a natural ligand or substrate. "Rational drug design" refers to replacing the natural ligand or substrate by an inert ligand, an inhibitor or some other molecule that alters the natural activity of the 30S ribosomal subunit.

As used herein, the term "determination of the structure" refers to the determination of the three dimensional structure of proteins by X-ray crystallography. Well ordered protein crystals contain multiple arrays of identical molecules that can diffract an X-ray beam giving a defined diffraction pattern from which the structure of the protein molecule can be deduced.

As used herein, the term "contacting" refers to the incubation of an inhibitor compound together with a 30S ribosomal subunit according to the invention under conditions where the inhibitor compound binds to the 30S ribosomal subunit with a dissociation constant as defined herein and in a manner that can be detected by a binding assay of the invention.

As used herein, "three dimensional structure" refers to the spatial arrangement of the 30S subunit polypeptide chains and 16S ribosomal RNA within a protein crystal. The three-dimensional structure of the 30S ribosomal subunit of the invention is defined by a set of structure coordinates as set forth in Table 1. The term "structure coordinates" refers to Cartesian coordinates derived from mathematical equations related to the patterns obtained on diffraction of a monochromatic beam of X-rays by the atoms (scattering centers) of a 30S ribosomal subunit in crystal form. The diffraction data are used to calculate an electron density map of the repeating unit of the crystal. The electron density maps are then used to establish the positions of the individual atoms of the 30S ribosomal subunit or 30S ribosomal subunit bound by a candidate modulator compound. Those of skill in the art will understand that a set of structure coordinates for a 30S ribosomal subunit or a portion thereof, is a relative set of points that define a shape in three dimensions.

As used herein, the term "resolution" refers to the resolution of the electron density map. The quality of protein crystals is determined by the ability of the crystal to scatter X-rays of wavelengths (typically 1.0 to 1.6 Angstroms) suitable to determine the atomic coordinates of the protein. The measure of the quality is determined as a function of the highest angle of scatter (the ultimate or intrinsic resolution). According to Bragg's Law: $\lambda = 2d \sin \theta$., where $\theta$ represents the reflection angle $\lambda$ the wavelength of the X-ray beam, and d the distance between two adjacent planes that are separated by the length of one of the unit cell axes. d therefore represents the resolution of the crystal form in angstroms and is routinely used to judge the ultimate usefulness of protein crystals.

As used herein, the term "higher resolution" refers to a resolution as defined herein of less than 5 Angstrom, preferably less than 3 Angstroms and most preferably equal to or less than 1.5 Angstroms.

As used herein, the term "lower resolution" refers to a resolution as defined herein of greater than 3 Angstroms, preferably greater than 4 Angstroms and most preferably equal to or greater than 5 Angstroms.

As used herein, the term "characterizing the binding" refers to characterizing the association of a modulator compound with the 30S ribosomal subunit that is detectable by a binding assay of the invention. As the term is used herein, binding is "specific" if it occurs with a $K_d$ of 1 mM or less, generally in the range of 500 µM to 10 pM.

As used herein, the term "inhibitor" refers to a compound that binds to the 30S ribosomal subunit with a dissociation constant, as defined herein, and decreases the translational activity of the associated ribosome by at least 10% when compared to the translation activity of the associated ribosome in the absence of inhibitor. According to the invention, "inhibitor" compounds are preferably antibiotics and derivatives thereof.

The term "translational activity" refers to any activity associated with a ribosome, containing the 30S ribosomal subunit, that is required for polypeptide chain synthesis. Translational activity is detected or measured in a translation assay as described herein.

The term "determining the activity" refers to detecting or measuring the translational activity of the ribosome as defined herein. Translational activity can be measured by a number of different assays known to those in the art including, but not limited to, assays that measure tRNA binding, mRNA binding and amino acid incorporation into a nascent polypeptide chain (as described in Ashraf, S. et al. RNA 5, 503–511; Von Ahsen, U. et al. (1997) RNA 3:49–56 and Zubay G Annu *Rev Genet* 1973;7:267–87).

The term "atomic model" refers to the proposed structure of the 30S ribosomal subunit that is deduced by matching the electron density map of the amino acid side chains obtained from X-ray diffraction data to the known sequence of the polypeptide chain.

The term "providing the structure of the 30S ribosomal subunit" refers to providing the three dimensional structure of the 30S ribosomal subunit as deduced from the atomic co-ordinates shown in Table 1.

The term "providing the structure of a candidate modulator molecule" refers to providing the three dimensional structure of a modulator compound as defined in commercially available computer databases, for example Available Chemical Directory (ACD) from the company MDL (U.S.), as well as various electronic catalogues of publicly available compounds such as the National Cancer Institute (NCI, U.S.) catalogue, ComGenex catalogue (Budapest, Hungary), Asinex (Moscow, Russia)

The term "resolving a structure" refers to interpreting an electron density map by superimposing onto it the 30S ribosomal subunit polypeptide chain and 16S RNA of known sequence and stereochemistry. The structure is said to be "resolved" if the electron density map of the 30S ribosomal subunit obtained from the X-ray diffraction data fits or matches the electron density of the polypeptide side chains as predicted from the polypeptide amino acid sequence.

The term "refining a model" refers to the process in which an atomic model is adjusted to minimize the difference between the experimentally observed diffraction amplitudes of a crystal, for example the 30S ribosomal subunit crystal, and those calculated for a hypothetical crystal containing the proposed model.

The term "species other than *thermophilis*" refers to species other than the bacterium *T. thermophilis* including other species of prokaryotes, preferably those species that are pathogenic for humans. These species include gram-positive strains (including but not limited to: *Streptococcus faecalis, Staphylococcus aureus, Streptococcus pneumoniae, Clostridium difficile*), gram-negative strains (including but not limited to: *Escherichia coli, Salmonella typhimurium, Haemophilus influenzae, Neisseria meningitis, Pseudomonas aeruginose, Entesobacter cleacae, Heliobacter pylori, Moraxella catarrhalis, Bacteriodes fragilis*) and others which fall into neither category (including but not limited to *Legionella pneumophila*).

The term "structure factor data" refers to structure factor amplitudes. Structure factor amplitudes represent the normalized amplitudes of the x-ray reflections (spots) that are measured directly in a diffraction experiment.

The term "deriving structure factor data from atomic coodinate data" refers to calculating the structure factors by a simple Fourier transform, using one of a number of standard programs including SFALL in the CCP4 package or CNS and the known coordinates, cell dimensions and space group derived from the X ray diffraction data.

The term "designing a compound" refers to using computer programs, known to those in the art (for example Catalyst (Accelrys) and Unity (Tripos)) to identify novel compounds, that are predicted to bind to functionally important regions of the 30S ribosomal subunit and may, therefore, act as modulators of ribosomal function.

The term "selecting a compound" means identifying and choosing potential modulator compounds from commercially available libraries, for example Available Chemical Directory (ACD) from the company MDL (U.S.) and online catalogues of publicly available compounds such as the National Cancer Institute (NCI, U.S.) catalogue, ComGenex catalogue (Budapest, Hungary), Asinex (Moscow, Russia) etc. Compounds are selected based on their ability to bind to functionally important regions of the 30S ribosomal subunit as predicted by computer docking programs as defined herein.

The term "comparing a structure" refers to the process of superimposing the electron density map of the 30S ribosomal subunit bound by a candidate modulator compound with the electron density map obtained with a 30S ribosomal subunit in the absence of the candidate modulator compound.

The term "characterizing an active site" refers to defining those residues of the 30S subunit that participate in, for example (1) the binding of a candidate modulator compound to the 30S ribosomal subunit; (2) tRNA binding; (3) mRNA binding; (4) polypeptide synthesis or (5) translocation. The structural components of active sites can include regions of the 30S ribosomal complex not directly associated with tRNA or mRNA or modulator compound binding but which are required for the ribosome to function, for example those regions which undergo structural changes associated with protein synthesis or are target sites for regulation by cofactors, phosphorylation or acetylation.

The term "difference Fourier electron density maps" refers to the electron density map obtained by subtracting the X-ray crystallographic diffraction data of the 30S ribosomal subunit in the presence of ligand from the X-ray crystallographic diffraction data of the 30S subunit in the absence of ligand.

The term "modelling the structure" refers to the examination of the interaction of 30S subunit binding partners and the known three dimensional structure of the 30S ribosomal subunit using docking programs such as GRAM, DOCK, or AUTODOCK [Dunbrack et al., *Folding & Design*, 2:27–42 (1997)]. Appropriate modification of the shape or chemical structure of a potential modulator can improve binding specificity and minimize repulsion and steric hindrance between the 30S subunit and the modulator.

The term "analyzing a 30S ligand complex" refers to the determination of 30S-ligand complex structure by defining the difference Fourier electron density maps as described herein.

The term "computer fitting model" refers to computer programs that are used to alter the structure of a candidate modulator compound so that it can bind stably and specifically and with minimal interference to a defined active site of the 30S ribosomal subunit.

The term "docking program" refers to computer software programs that are used to predict the structure of a 30S-ligand complex. A number of docking programs can be used (Jones, G. and Willett, P. (1995). Docking small-molecule ligands into active sites. *Curr Opin Biotechnol*, 6(6), 652–6.), for example, AutoDock is a suite of automated docking tools that are designed to predict how small molecules, such as substrates or drug candidates, bind to a receptor of known 3D structure. An alternative program, the Global Range Molecular Matching (GRAMM) methodology, relies on an empirical approach to smoothing the intermolecular energy function by changing the range of the atom-atom potentials. The technique locates the area of the global minimum of intermolecular energy for structures of different accuracy. The quality of the prediction, however, depends on the accuracy of the structures.

The term "activity of a binding partner" refers to the ability of a binding partner to increase or decrease the translational activity of a ribosome containing a 30S ribosomal subunit by at least 10% when bound to the 30S ribosomal subunit as compared to the translational activity of a ribosome containing the 30S ribosomal subunit in the absence of binding partner.

The 30S Crystal Structure.

The high resolution structure provided herein provides a crystal with unit cell dimensions which are provided in the accompanying tables 1–4 to 3 decimal places, as set out above. However, those of skill in the art wishing to reproduce the crystallization described herein and obtain such crystals will appreciate that a degree of experimental variability and error will mean that crystals of the invention will be obtained with a unit cell dimension within, but not exactly corresponding to, this size. Thus, crystals of the invention may generally be defined as having unit cell dimensions a, b, and c as defined above which vary in the case of a by ± about 4.0 Å, b by ± about 4.0 Å and c by ± about 5.0 Å, preferably a by ± about 1.0 Å, b by ± about 1.0 Å and c by ± about 2.0 Å. More preferably the variance is no more than a ± about 0.7 Å, b ± about 0.7 Å and c ± about 1.4 Å, and even more preferably no more than a ± about 0.2 Å, b ± about 0.2 Å and c ± about 0.4 Å. These unit cell sizes are believed to define novel and more highly resolved unit cell sizes than has previously been possible in the art.

Table n

The coordinates of Tables 1 to 4 provide a measure of atomic location in Angstroms, to a third decimal place. In order to use the information in these Tables for the purposes described herein as being aspects of the present invention, these coordinates may be varied by up to about ±1.0, such as by up to about ±0.7, preferably no more than up to about ±0.5 Angstroms, without departing from the scope of the invention.

Furthermore, varying the relative atomic positions of the atoms of the structure so that the root mean square deviation of the 16S RNA or S2–S20 protein backbone atoms is less than about 1.5 Å (preferably less than about 1.0 Å and more preferably less than about 0.5 Å) when superimposed on the coordinates provided in Table n for these structures, will generally result in a structure which is substantially the same as the structure of Table n respectively in terms of both its structural characteristics and potency for structure-based drug design of 30S ligands.

Thus, for the purposes described herein as being aspects of the present invention, it is within the scope of the invention if: the coordinates of Table n are transposed to a different origin and/or axes; the relative atomic positions of the atoms of the structure are varied so that the root mean square deviation of conserved residue backbone atoms is less than about 1.5 Å (preferably less than about 1.0 Å and more preferably less than about 0.5 Å) when superimposed on the coordinates provided in Table n for the conserved residue backbone atoms; and/or the number and/or positions of water molecules is varied. Reference herein to the use of the coordinates of Table n thus includes the use of coordinates in which one or more individual values of the Table are varied in this way.

Table n includes coordinates of metal ions which are selected from zinc, cobalt and magnesium. Some or all of these ions may optionally be discarded from the Tables when using the data. The Tables also list the coordinates of a 26 amino acid peptide, Thx, as well as a 6 nucleotide fragment of mRNA, NNNUCU, designated as molecule X. Both the coordinates of both these molecules may likewise optionally be discarded, i.e. so that the coordinates of the 16S RNA and the proteins S2 to S20 alone are modeled and used in applications of the invention.

There are a few N- or C-terminal sequences of the S2 to S20 proteins which were not resolved in the structure of Table n, together with some of the 5' and 3' residues of the 16S RNA. These are not essential for the purposes of the present invention.

This invention provides those of skill in the art a means to provide 30S crystals of *T. thermophilus*. The conservation of ribosome structure, particularly regions of structure essential for function, between prokaryotes, for example prokaryotes which are human pathogens, such as *Staphylococcus* spp, and the like, allows the structure herein to be useful in the provision of anti-bacterial agents in general. Thus, the structures may be used to solve 30S subunits by the technique of molecular replacement. In such a method, x-ray diffraction data are obtained from crystals of a 30S subunit from another species, e.g. a species of a bacteria pathogenic to humans. The coordinates of Table n may be used to find the orientation of the unknown molecule in the crystal, and electron density maps calculated. These maps can then be interpreted with the sequence of the species in question, and the coordinates of the 30S structure can be used to help and speed interpretation. In this way, the structure of the 30S facilitates the determination of structures of 30S subunits and whole ribosomes from other organisms.

Accordingly, the invention provides a method for the determination of the structure of a bacterial 30S from a species other than *T. thermophilus* which method comprises:

(a) crystallising the 30S of the species to obtain a crystal;

(b) performing X-ray crystallography on the crystal to obtain X-ray diffraction data;

(c) providing the structure data of Table n; and (d) using molecular replacement to calculate an electron density map of the 30S.

The crystallization step (a) is optionally performed with an antibiotic Z, either in a co-crystallization or by soaking the antibiotic following crystal formation. Thus, the calculated electron density map may be that of the 30S—antibiotic complex.

In such a method the 30S may be prepared by removal of the S1 subunit, as described herein.

The electron density map obtained may then be used to calculate the atomic coordinate data of the 30S, optionally with bound antibiotic Z. The atomic coordinate data thus obtained may be used to for the design and analysis of new and specific ligands for 30S as described herein.

Production of Crystals.

Selective removal of the S1 subunit protein facilitates the generation of crystals according to the invention. A suitable method for the selective removal of the S1 subunit protein involves the use of a hydrophobic interaction chromatography column (poros-ET). 30S ribosomal subunits lacking the S1 subunit may suitably be separated from those containing the S1 subunit by running a column using a reverse ammonium sulfate gradient from 1.5M to 0.5M, with 20 mM Hepes, pH 7.5, and 10 mM acetate. The 30S subunits lacking S1 are eluted first, giving the first major peak. During elution of the 30S peak the ammonium sulfate concentration is maintained at a constant level. Once the 30S peak has eluted the ammonium sulfate concentration is then further reduced to elute the 30S+S1 fraction.

An alternative method for the selective removal of the S1 subunit protein is by preparative sepharose or by gel electrophoresis. Gel electrophoresis may suitably be carried out by first preparing and mixing a 3% acrylamide, 0.5% agarose cylindrical gel, and pouring this gel into a BioRad Prep Cell. 30S ribosomal subunits are then loaded onto the gel and continuously eluted as they emerge form the other end of the gel. The 30S fraction lacking the S 1 subunit comes off first, giving the first major peak. The 30S+S1 fraction gives the trailing peak (or shoulder) and can be discarded.

Selective removal of the S1 ribosomal subunit can also be achieved by poly-U sepharose chromatography followed by extensive salt washing as described in A. R. Subramanian, Rienhardt, P., Kimura, M. and Suryanarayana, T. (1981): Fragments of Ribosomal Protein S1 and its mutant Form m1S1: Localization of Nucelic Acid Binding Domains in the Middle Region of S1. *Eur. J. Biochem.* 119, 245–249 and B. Subramanian, A. R., (1983): Structure and Functions of Ribosomal Protein S1. In Progress in Nucleic Acid Research and Molecular Biology, v. 28, W. E. Cohn, (ed.) 101–142. *Academic Press,* New York. (described on page 104).

Once the S1 is removed, the crystals may be formed, using suitable conditions. These include the use of 13–17% v/v methyl-2,4-pentanediol in the presence of 200–300 (e.g. about 250) mM KCl, 50–100 (e.g. about 75) mM ammonium chloride, 15–30 (e.g. about 15 or about 25) mM $MgCl_2$ at a pH of 6.0–7.5 (e.g about pH 6.3–6.7 such as pH 6.5) in 50–150 (e.g. about 100) mM sodium or potassium cacodylate or MES (2-(N-morpholino) ethane sulphonic acid).

In a particular aspect, the conditions may comprise the use of 250 mM KCl, 75 mM $NH_4Cl$, 25 mM $MgCl_2$, 6 mM 2-mercaptoethanol in 0.1 M potassium cacodylate or 0.1 M MES (2-N-morpholino-ethanesulfonic acid) at pH 6.5 with 13–17% MPD as the precipitant.

The crystals may be grown by any suitable method known as such to those of skill in the art. Suitably, the crystals may be grown over a period of 4–8 weeks at about 4° C. Once crystals are obtained, the antibiotic Z may be soaked into the crystals. The antibiotic may be used in any convenient soluble form at a concentration range of from about 10 to about 500 μM, preferably from about 50 to about 100 μM, such as about 80 μM. The structure of the crystals so obtained may be resolved, and crystals which resolve to a resolution of at least about 3 Å selected. Crystals which resolve to a resolution of at least about 3 Å obtainable by such a method are a further aspect of the invention.

Uses of the Structural Data of Table n

The determination of the three-dimensional structure of 30S provides a basis for the design of new and specific ligands for 30S. For example, knowing the three-dimensional structure of 30S, computer modelling programs may be used to design different molecules expected to interact with possible or confirmed active sites, such as binding sites or other structural or functional features of 30S.

Modelling of Candidate Compounds

The high resolution models of the 30S provided by Table n can be used to examine and determine the binding of the antibiotics paromomycin, streptomycin, spectinomycin, tetracycline, pactamycin and hygromycin B to the 30S ribosome, and by using this information, the skilled person in the art can design ligand which may compete with these antibiotics and which can overcome the resistance of bacterial cells to these antibiotics.

A candidate ligand, particularly but not necessarily, one which acts as an inhibitor molecule may be any available compound. A number of commercial sources of libraries of compound structures are available, for example the Cambridge Structural Database, the Chemical Directory (ACD) from the company MDL (U.S.) as well as various electronic catalogues of publicly available compounds such as the National Cancer Institute (NCI, U.S.) catalogue, ComGenex catalogue (Budapest, Hungary), Asinex (Moscow, Russia) etc. Such libraries may be used to allow computer-based high throughput screening of many compounds in order to identify those with potential to interact with the active site of a ribosome.

More specifically, a potential ligand capable of modulating 30S activity can be examined through the use of computer modelling using a docking program such as GRAM, DOCK, or AUTODOCK (see Walters et al., *Drug Discovery Today,* Vol.3, No.4, (1998), 160–178, and Dunbrack et al., *Folding and Design,* 2, (1997), 27–42) to identify potential ligands of 30S. This procedure can include computer fitting of potential ligands to 30S to ascertain how well the shape and the chemical structure of the potential ligand will bind to the enzyme.

Also computer-assisted, manual examination of the active site structure of 30S may be performed. The use of programs such as GRID (Goodford, *J. Med. Chem.,* 28, (1985), 849–857)—a program that determines probable interaction sites between molecules with various functional groups and the enzyme surface—may also be used to analyse the active site to predict partial structures of ligands for the site.

Computer programs can be employed to estimate the attraction, repulsion, and steric hindrance of the two binding partners (e.g. the 30S and a potential ligand). Generally, the tighter the fit, the fewer the steric hindrances, and the greater the attractive forces, the more potent the potential ligand since these properties are consistent with a tighter binding constant. Furthermore, the more specificity in the design of a potential ligand, the more likely it is that the ligand will not interact with other proteins as well. This will tend to minimise potential side-effects due to unwanted interactions with other proteins.

In one aspect, the above described methods may be used to perform a computer-based method of rational drug design which comprises:

(i) providing the structure of the 30S ribosome defined by the coordinates found in Table n;

(ii) providing the structure of a candidate inhibitor molecule;

(iii) fitting the candidate to the structure of the 30S to provide a result; and (iv) comparing the result with a structure comprising the 30S of the Table together with the antibiotic coordinate data of the Table.

In the case where Table n is Table 2 (tetracycline), the comparison may be with one or other, or both, bound tetracycline molecules.

The 30S ribosome used in the present invention comprises an additional small protein molecule, Thx, as well as a short sequence of nucleotides designated molecule X. It will be understood that the phrase "the structure of the 30S ribosome as defined by the coordinates of Table n" and the like (where n is any one of 1 to 4) as used above and elsewhere herein is reference to the coordinates defined by atoms of the 16S RNA and proteins S2 to S20 of the Table n, including or not including the Thx and molecule X coordinates, optionally in conjunction with any or all of the metal ions defined by Table n.

The data of Table n indicate that the primary contacts between antibiotic Z and the 30S are mediated by the 16S RNA. Thus, in the above aspect of the invention, those of skill in the art may choose to use the data of Table n relating to the 16S RNA and one of the antibiotics Z in the process of drug design. Accordingly, there is also provided a computer-based method of rational drug design which comprises:

(i) providing the structure of the 16S RNA of the 30S ribosome as defined by the coordinates of Table n;

(ii) providing the structure of a candidate inhibitor molecule;

(iii) fitting the structure of candidate to the structure of the 16S RNA of the 30S to provide a result; and (iv) comparing the result with a structure comprising the 16S RNA of the 30S of the Table together with the antibiotic structure of the Table.

In an alternative aspect, the method of the invention may utilise the coordinates of atoms of interest of the 30S which are in the vicinity of an antibiotic Z binding region in order to model the pocket in which Z binds. These coordinates may be used to define a space which is then screened "in silico" against a candidate inhibitor molecule. Thus, the invention provides a computer-based method of rational drug design which comprises:

(i) providing the coordinates of at least one atom of Table n of the 30S ribosome; providing the structure of a candidate inhibitor molecule;

(ii) fitting the structure of candidate to the coordinates of the 30S ribosome provided to obtain a result; and (iii) comparing the result with a structure comprising the coordinates of the 30S ribosome provided and at least one atom from one antibiotic structure of Table n.

In this embodiment, the at least one atom of the 30S ribosome provided will preferably be within a distance of about 50, preferably about 10 Angstroms of at least one of the atoms of any of the antibiotic molecule described in Table n.

In practice, it will be desirable to model a sufficient number of atoms of the 30S ribosome as defined by the coordinates of Table n which represent a binding pocket. Binding pockets and other features of the interaction of antibiotic Z with the 30S ribosome are described in the accompanying examples. Thus, in this embodiment of the invention, there will preferably be provided the coordinates of at least 5, preferably at least 10, more preferably at least 50 and even more preferably at least 100 atoms such as at least 500 atoms and most preferably at least 1,000 atoms of the 30S ribosome. Of these atoms provided, at least one will preferably be within the distance mentioned above of the antibiotic molecules described in Table n.

Likewise, when a candidate is fitted to the selected coordinates of the 30S ribosome the comparison with antibiotic is preferably made by reference to at least 3, such as at least 5, for example at least 8, more preferably at least 16 of the atoms of any of the antibiotic Z structures provided in Table n.

In another aspect, the method of the invention may utilise a sub-domain of interest of the 30S which is in the vicinity of a antibiotic binding region. Thus, the invention provides a computer-based method of rational drug design which comprises:

(i) providing the coordinates of at least a sub-domain of the 30S ribosome;

(ii) providing the structure of a candidate inhibitor molecule;

(iii) fitting the structure of the candidate to the coordinates of the 30S ribosome sub-domain provided to obtain a result; and (iv) comparing the result with a structure comprising the coordinates of the 30S ribosome of same sub-domain provided and at least one atom from the antibiotic Z structure of Table n.

In a further aspect, the accompanying examples and drawings show the specific sites of interaction of the antibiotic Z with the 30S ribosome. These data may be used to design ligands which interact with at least one of the sites of interaction of each identified antibiotic Z, and preferably at least about 50% of the sites of interaction identified for each separate antibiotic Z in each of FIGS. 1 to 6. Such ligands may be designed by:

(i) providing atomic coordinate data for at least one of the following nucleic acid or amino acid residues of the 30S:

Group I: G1405, A1408, C1490, G1491, A1493, G1494 and U1495;

Group II: G1064, C1066, G1068 and C1192;

Group III: U14, C526, G527, A913, A914, C1490, G1941 and S12Lys45;

Group IV: A965, G966, G1053, C1054, C1195, U1196, G1197 and G1198;

Group V: U244, A892 and C893;

Group VI: G693, A694, C788, C795, C796, S7Gly81 and optionally U1540;

Group VII: C1403, G1405, G1494, U1495, C1496 and U1498, (ii) providing a potential ligand; and (iii) fitting the ligand to the 30S to determine the interaction of the ligand with at least one chemical group present in the nucleic acid or amino acid residue of the selected group.

Preferably at least half the members of each group are used, and more preferably from half to t members of each group are used, where t represents a number which is more than half and at least T, preferably T-1 and more preferably T-2 where T is the total number of members of each group, subject to the requirement that t is greater than T/2 (i.e. for group II 2, 3 or 4 members may all be used, and for group V, 2 or 3 members may be used).

In another aspect, in place of in silico methods, high throughput screening of compounds to select compounds with ribosome binding activity may be undertaken, and those compounds which show ribosome binding activity may be selected as possible candidate inhibitors, and further crystallized with 30S (e.g. by co-crystallization or by soaking) for x-ray analysis. The resulting X-ray structure may be compared with that of Table n for a variety of purposes. For example, where the contacts made by such compounds overlap with those may by antibiotic Z, novel molecules comprising residues, which contain contacts of both Z, and the other inhibitor may be provided.

Having designed or selected possible binding ligands, these can then be screened for activity. Consequently, the method preferably further comprises the further steps of:

(i) obtaining or synthesising the potential ligand; and (ii) contacting the potential ligand with 30S to determine the ability of the potential ligand to interact with 30S.

More preferably, in the latter step the potential ligand is contacted with 30S under conditions to determine its function, for example in a cell free translation system. Such conditions (including cell free translation systems) are known in the art.

Instead of, or in addition to, performing such an assay, the method may comprise the further steps of:

(i) obtaining or synthesising the potential ligand;

(ii) forming a complex of 30S and the potential ligand; and (iii) analysing the complex by X-ray crystallography to determine the ability of the potential ligand to interact with 30S.

Detailed structural information can then be obtained about the binding of the potential ligand to 30S, and in the light of this information adjustments can be made to the structure or functionality of the potential ligand, e.g. to improve binding to the active site. These steps may be repeated and re-repeated as necessary.

Another aspect of the invention includes a compound, which is identified as an ligand of 30S by the method of the above aspects of the invention.

In another aspect, the invention provides a method of analysing a 30S-ligand complex wherein the ligand has been obtained by the methods of the invention described above, comprising the steps of:

(i) co-crystallizing the 30S with the ligand or soaking the ligand into crystals of the 30S;

(ii) collecting X-ray crystallographic diffraction data from the crystals of the 30S-ligand complex;

(iii) using the three-dimensional structure of 30S of Table n, or at least one sub-domain thereof, to generate a difference Fourier electron density map of the 30S-ligand; and (iv) modelling the ligand in the difference Fourier electron density.

Therefore, 30S-ligand complexes can be crystallised and analysed using X-ray diffraction methods, e.g. according to the approach described by Greer et al., *J. of Medicinal Chemistry*, Vol. 37, (1994), 1035–1054, and difference Fourier electron density maps can be calculated based on X-ray diffraction patterns of soaked or co-crystallized 30S and the solved structure of uncomplexed 30S. These maps can then be used to determine the structure of the ligand bound to the 30S and/or changes the conformation of 30S.

Data obtained from a ligand bound to 30S may be used to improve the ligand, for example by adding or removing functional groups, substituting groups or altering its shape to obtain improved candidates, which may then be screened, solved in complex as described herein above, in an iterative process.

Electron density maps can be calculated using programs such as those from the CCP4 computing package (Collaborative Computational Project 4. The CCP4 Suite: Programs for Protein Crystallography, *Acta Crystallographica*, D50, (1994), 760–763). For map visualisation and model building programs such as "O" (Jones et al., *Acta Crystallograhy*, A47, (1991), 110–119) can be used.

The high resolution data provided herein allows those of skill in the art who have obtained structures of worse resolution of the 30S to refine such structures in the light of the data of Table n. Thus, in a further aspect, the invention provides a method for modelling a structure of a 30S ribosome which comprises providing an atomic model of a structure at a resolution of worse than about 3 Å (e.g. a resolution of worse than about 5 Angstroms, such as about 5–12 Å), comparing the structure obtained with the data of Table n, and refining the model obtained to resolve the structure in order to provide a higher resolution structure. Such a process will be useful for the refinement of a 30S itself, or the 30S in various functional states as part of the 70S ribosome (e.g. bound to mRNA, elongation factors or the like).

Such a method will be useful in providing the structure of the 30S ribosome from other bacterial sources, since the overall secondary and tertiary structure of such ribosomes will be highly conserved in comparison to the *T. thermophilus* structure provided herein. The data provided herein may be used in a process of modelling the 30S of other species ab initio by homology modelling using energy minimization criteria.

By providing such computer readable media, the atomic coordinate data can be routinely accessed to model 30S or a sub-domain thereof. For example, RASMOL is a publicly available computer software package which allows access and analysis of atomic coordinate data for structure determination and/or rational drug design.

On the other hand, structure factor data, which are derivable from atomic coordinate data (see e.g. Blundell et al., in *Protein Crystallography, Academic Press*, New York, London and San Francisco, (1976)), are particularly useful for calculating e.g. difference Fourier electron density maps.

In another aspect, the present invention provides systems, particularly a computer systems, intended to generate structures and/or perform rational drug design for 30S ligand complexes, the systems containing either (a) atomic coordinate data according to Table n, the data defining the three-dimensional structure of 30S or at least one sub-domain thereof, or (b) structure factor data for 30S, the structure factor data being derivable from the atomic coordinate data of Table n.

Mutant strains resistant to the action of these antibiotics can arise through mutation of a protein subunit of the 30S or through mutation or modification in the 16S RNA (e.g. 2'O-methylation), or modification (e.g. acetylation) of the antibiotic). The sites of mutations in some cases are known or can be identified. Where such sites are identified through, for example, primary sequence data, the invention provides a means to model the structure of the mutants.

There is thus provided a method which comprises providing the structure of the 30S ribosome of Table n, changing one amino acid or nucleotide of the structure to provide a mutant 30S, and modeling the structure of the mutant 30S to provide a structure of the mutant. The mutant may be used in the manner described above for the wild type, e.g. stored in computer readable form, modeled to provide ligands, and the like. The modeling may be based upon the predicted behavior of the atoms of the changed amino acid based upon its interaction with the surrounding atoms in the model provided herein.

This process may be iterative, e.g. to produce successive mutations into the 30S structure, for example 2, 3, 4, or 5 to 10 mutations or more.

Regions of 30S which may be subject to this aspect of the invention include but are not limited to those regions identified in the accompanying examples as regions of the 30S involved in binding to antibiotics.

In a further aspect, the present invention provides a means to solve or interpret electron density maps of the whole 70S ribosome at low or high resolution, and thus, solve the structure of the whole 70S ribosome.

In particular, the invention provides a method for the determination of the structure of a bacterial 70S ribosome which method comprises:

(i) crystallizing the 70S of the species to obtain a crystal;

(ii) performing X-ray crystallography on the crystal to obtain X-ray diffraction data;

(iii) providing the structure data of Table 1; and (iv) using molecular replacement to calculate an electron density map of the 70S.

The crystallization step (a) is optionally performed with an antibiotic Z, either in a co-crystallization or by soaking the antibiotic following crystal formation. Thus, the calculated electron density map may be that of the 30S—antibiotic complex.

The invention is illustrated, but not limited, below by the following examples, their accompanying Figures and Tables. In Table n there is shown in each row Atom number, element type, residue (amino acid, nucleotide, etc.), number in molecule (for proteins N to C terminal direction, for nucleic acid 5' to 3' direction), X, Y and Z co-ordinates, occupancy, B factor ($Å^2$) and an identifier for the member of the 30S.

Throughout the accompanying example, the numbering system for *E. coli* 16S RNA, as well as the standard helix numbering, denoted H1–H45, for the secondary structure elements [19] is used with some modifications as shown in FIG. 1. The most significant differences between the *E. coli* and *T. thermophilus* sequences are a shorter H6 and H10, and insertions in H9 and H33a. Any insertions in *T. thermophilus* relative to *E. coli* are indicated in the coordinates with an insertion letter after the nucleotide number, following the practice for tRNA.

Crystallization of Paromomycin, Spectinomycin and Streptomycin to the 30S Ribosome, Data Collection and Structure Determination.

Crystallization of Paromomycin, Spectinomycin and Streptomycin to the 30S Ribosome 30S crystals completely lack ribosomal protein S1. S1 was, therefore, selectively removed from the 30S ribosomal subunit prior to crystallization. Crystals were obtained in 13–17% MPD over a range of pH in the salt and magnesium conditions described by Trakhanov et al [3]. The crystals were largest and most reproducibly obtained at a pH of 6.5 in 0.1 M cacodylate or MES buffer. Crystals took approximately 6 weeks at 4° C. to grow to their maximum size. The largest crystals, which were required for high resolution data collection, grew to a size of 80–100×80–100×200–300 microns. The activity of redissolved crystals in poly(U)-directed protein synthesis was comparable to that of freshly isolated 30S subunits.

Data Collection

Crystals were transferred to 26% MPD by vapor diffusion in two steps over a period of 6 days. All crystals (except for those soaked in osmium hexammine or osmium pentammine) also contained 1 mM cobalt hexammine in the cryoprotectant. Crystals were flash-cooled by plunging into liquid nitrogen, and data collection was done in a cryostream at 90–100 K.

A large fraction of crystals was screened at beamlines 9.6 or 14.1 at the SRS at Daresbury Laboratories, using two short exposures at least 40 degrees apart. These crystals were then analyzed for diffraction limits, cell dimensions and mosaic spread. Only crystals of similar cell dimensions and with reasonable mosaic spread were used for data collection.

Potential derivatives were screened on beamlines X25 at the NSLS at Brookhaven National Laboratory and BM-14 at the ESRF (Grenoble). Data to about 4.5 Å were obtained from X25. High resolution data were collected at SBC ID-19 at the APS in Argonne National Laboratory, and ID14-4 at the ESRF. In all cases, derivative data were collected at the peak of the fluorescence at the LIII edge to maximize anomalous differences. At X25 and SBC ID-19, the kappa goniostat was used to rotate precisely about a mirror plane so that small anomalous differences could be measured accurately. Each crystal typically yielded 3–10 degrees of data. Data were integrated and scaled using HKL-2000 [10].

Structure Determination

Previously determined phases at 5.5 Å [9] were used to locate heavy atom sites using anomalous difference Fourier maps. Initially, these sites were used for phasing to 3.35 Å using the program SOLVE [11], followed by density modification with SOLOMON [12], using the procedure implemented in SHARP [13]. Optimization of the various parameters in the procedure was required to obtain interpretable maps. The RNA and some of the proteins were built using the SOLVE maps. The sequence of *Thermus thermophilus* 16S RNA [14] was used for the structure. For proteins, a combination of previously published sequences and new ones from the Göttingen *Thermus* genome sequencing project were used. Improved maps were obtained by calculating experimental phases to 3.2 Å using SHARP followed by density modification and phase extension to 3.05 Å with DM [15]. The improved maps allowed us to build all the ordered parts of the structure. The model was built using O [16], and refined using the program CNS [17]. Maximum likelihood refinement was used, initially with both amplitudes and experimental phase probability distributions to 3.35 Å, and subsequently with amplitudes to 3.05 Å.

The 30S subunit from *Thermus thermophilus* consists of a 1522 nucleotide 16S ribosomal RNA [14] and 21 associated proteins, of which 20 have known counterparts in *E. coli*. Protein S21 is not present in *Thermus*, and protein S1 has been removed from the 30S prior to the crystallization. In addition, a 26 residue peptide, Thx, is present in *Thermus* 30S subunits [18].

Experimentally phased maps clearly showed main chain density for RNA and protein, individual bases (which were often of sufficient quality to distinguish purines from pyrimidines), and large well-ordered side chains of proteins. These maps were used to build 16S RNA and the previously unknown proteins S2, S3, S9, S10, S11, S12, S13, S14 and Thx. In addition, regions that were disordered in isolated structures or had changed significantly were also built. This often consisted of significant portions of the N- and C-terminal tails of the proteins, sometimes including entire domains that were unfolded in isolation. Proteins with small cores and long loops, such as S16 and S17, had to be substantially rebuilt, since these loops were generally disordered in the solution NMR structures. Finally, the entire structure was rebuilt after an initial round of refinement. The current model consists of nucleotides 5–1511 of *Thermus thermophilus* 16S RNA (corresponding to 5-1534 of *E. coli* 16S RNA) and all of the ordered regions of the associated 20 proteins. The current model has been refined against 3.05 Å data with a conventional R-factor of 0.213, a free R-factor of 0.256 and good geometry. For the proteins, 94% of the residues were in the core or allowed regions of the Ramachandran plot, 3.9% in the generously allowed region and 1.8% in the disallowed region.

Crystallization of Paromomycin to the 30S Ribosome

Paromomycin is a member of the aminoglycoside family of antibiotics which increases the error rate of the ribosome. This family is thought to reduce the dissociation rate of A-site tRNA from the ribosome. Recent experiments suggest that it affects both initial selection and proofreading. Crystals were obtained and the data collected is provided in Table 1. FIG. 1 shows the interactions between 16S RNA residues and paromomycin.

Paromomycin binds in the major groove of H44 in a location that is in agreement with mutagenesis and protection data. It is also in general agreement with an NMR structure of paromomycin bound to an RNA fragment corresponding to its binding site [20]. Contacts are shown in FIG. 1. Ring IV contacts the backbone of both sides of helix in an orientation that differs from the NMR structure, while ring III makes only weak contacts with the RNA. Ring II forms tight interactions with both bases and backbone of the RNA, while Ring I inserts into the RNA helix and helps flip out bases A1192 and A1493 when compared to the structure in the absence of paromomycin. Ring I mimics a nucleotide base, stacking against G1491 and hydrogen-bonding with A1408. In addition it forms a tight H bond interaction with the phosphate backbone of A1493 which helps lock the flipped out bases in place. Except as noted, many of the interactions are similar to those reported in the NMR structure [20] although the bases are flipped out to a far greater degree, and consequently, a base pairing between A1408 and A1493 is not detected.

The codon and anticodon in the A site was modelled using a superposition of the 7.8 Å structure of the 70S ribosome with tRNA and mRNA bound. The flipped out bases point directly into the A site and are positioned to interact with the minor groove of the helix formed by the codon-anticodon interaction. It is probable that the A-site codon-anticodon helix must undergo some degree of rotation during or after GTP hydrolysis by EF-Tu, in a conformational change to a proofreading state of the decoding site. However, there are rather strict covalent and steric constraints on the A-site anticodon and especially the codon, which is covalently attached to both the P-site codon and downstream message. Thus, despite some rotational uncertainty in the orientation of the codon-anticodon helix, it appears unlikely that the 1492–1493 bases could interact with any portion of the codon-anticodon helix other than its minor groove, though interactions with other portions of the A-site tRNA anticodon loop are not ruled out. This model provides clues as to how paromomycin increases the affinity of the A site for tRNA. It seems likely that in the absence of paromomycin some energy is required to flip out A1492–A1493 so they can contact the tRNA, and presumably this energetic cost is compensated by the formation of favourable interactions with tRNA. By binding to H44, paromomycin forms a structure in which these bases are already flipped out, thus reducing the energetic cost of both cognate and non-cognate tRNA binding and increasing tRNA affinity for the A site.

This structure is in general agreement with a previously proposed model in which A1492 and A1493 would make contact with the minor groove of the mRNA-tRNA duplex [21]. In that model, it was suggested that these bases hydrogen bond with the 2'-OH of the message. Given the rotational uncertainty of the positioning of the A-site tRNA in the model, the hydrogen bonding of the adenines to the message was not determined. However, two scenarios appear possible, within the limits of the model. The adenines may hydrogen-bond to 2' OH groups of only the tRNA anticodon stem-loop, or they may hydrogen-bond to 2'OH groups of both the tRNA and the message. Both possibilities are attractive because they offer a direct explanation for increased affinity (and lower dissociation rate) of tRNA in the presence of the antibiotic. Finally, the degree to which the bases are flipped out in the structure allows a possible reconciliation of the proposal that the mRNA binds in the major groove of H44 23 with the notion that A1492 and A1493 inspect the minor groove of the codon-anticodon interaction.

Rings I and II of paromomycin are found in a number of other antibiotics including gentamycin. An NMR structure of gentamycin bound to the same fragment of H44 showed that these two rings interact with RNA in the same way as in paromomycin [20]. This suggests that other aminoglycosides that bind to the decoding centre on H44 induce errors in translation by the same mechanism as paromomycin.

Crystallization of Spectinomycin to the 30S Ribosome

Figure 2:
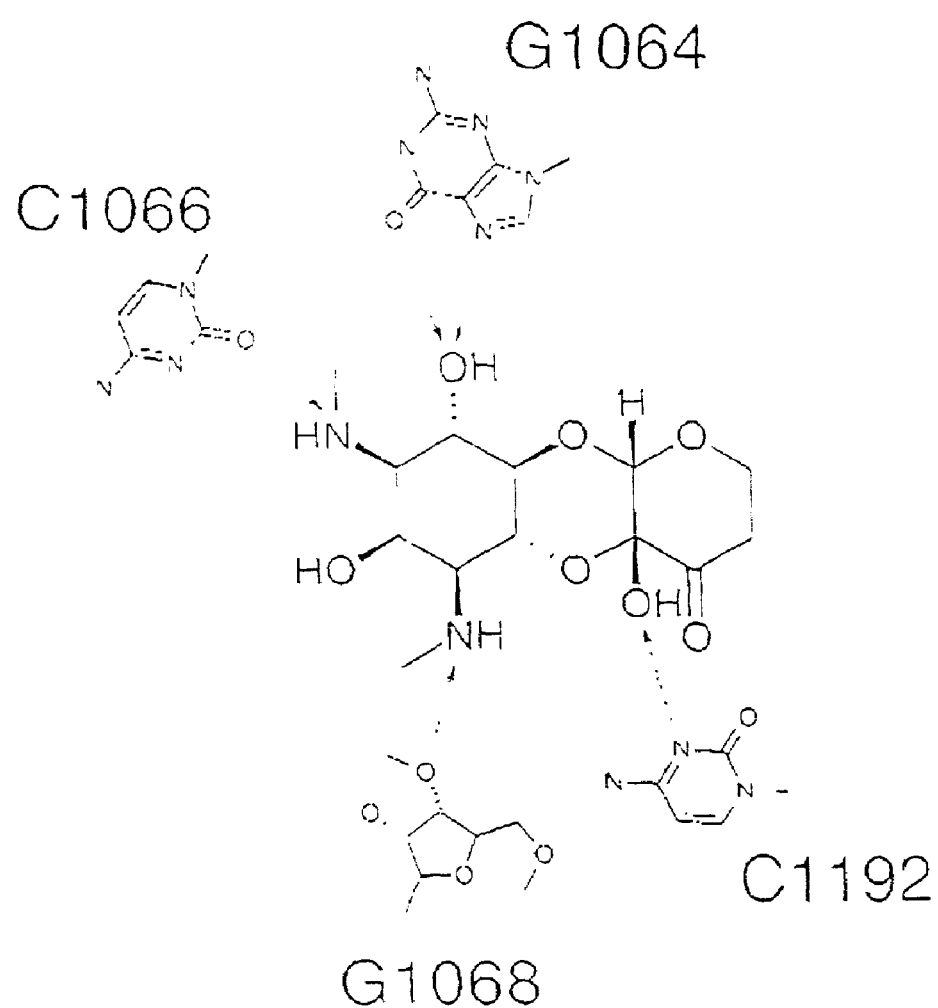
FIG. 2 shows the binding of spectinomycin to the 30S ribosome.

In contrast to the flexible aminoglycosides, the fused ring system in spectinomycin makes it a rigid molecule. It binds in the minor groove at one end of H34. It makes a single contact with a backbone phosphate and makes hydrogen bonds to a number of bases (FIG. 2). The most interactions are made with G1064 and C1192, consistent with protection studies [22] and mutagenesis data which showed that any combination of substitutions at these bases gave resistance to spectinomycin [23]. These two bases are held too far apart to form Watson-Crick base pairs, but are able to make a single hydrogen bond.

A loop of S5 and part of H28 of 16S RNA approach the spectinomycin binding site, but in this state do not make direct contacts with it. It is possible, however, that in other conformations of the 30S, spectinomycin is in more direct contact with these regions.

A superposition of the A, P and E site tRNAs from the 70S ribosome onto the 30S structure shows that a number of highly specific contacts from the head stabilize these tRNAs. A movement of tRNA from one site to the other must necessarily involve movement of elements of the head. Such movements would involve H34 and a possible rearrangement of the connections between it and helices 35 and 38. The structure suggests that the rigid spectinomycin molecule binds near this pivot point of the head and sterically blocks movement although it is also possible that it acts to stabilize the upper stem of H34 [23]. As mentioned above, mutations in S5 that cause resistance to spectinomycin [24] do not make direct contacts with the antibiotic. Rather, they map to a loop that stabilizes the interaction between H1 and the H35–H36 region, which is directly connected to H34. An attractive hypothesis is that the mutants destablize this interaction, and by thus removing the network of interactions that stabilizes the conformation of the head to the body via S5, allows it to move even when spectinomycin is bound.

Crystallization of Streptomycin to the 30S Ribosome

Figure 3:
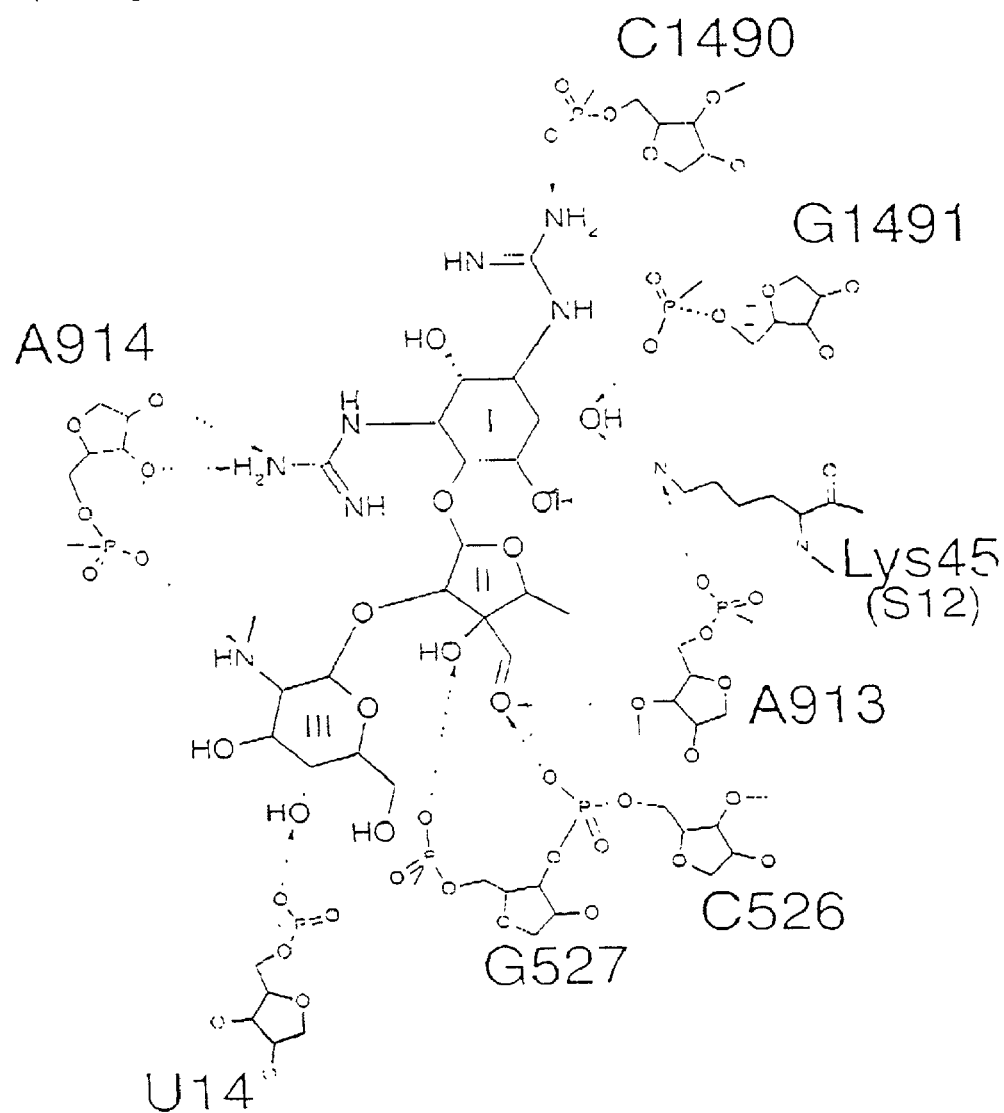
FIG. 3 shows the binding of streptomycin to the 30S ribosome.
Figure 4A:
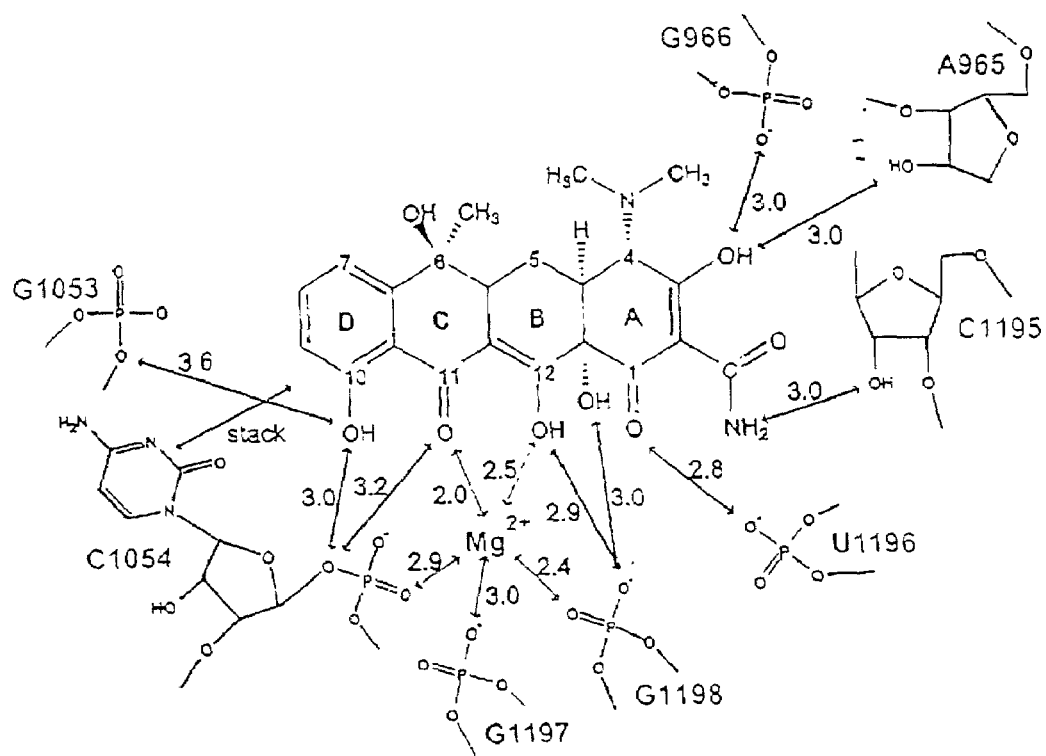
FIG. 4A shows the binding of tetracycline (primary site) to the 30S ribosome.
Figure 4B:
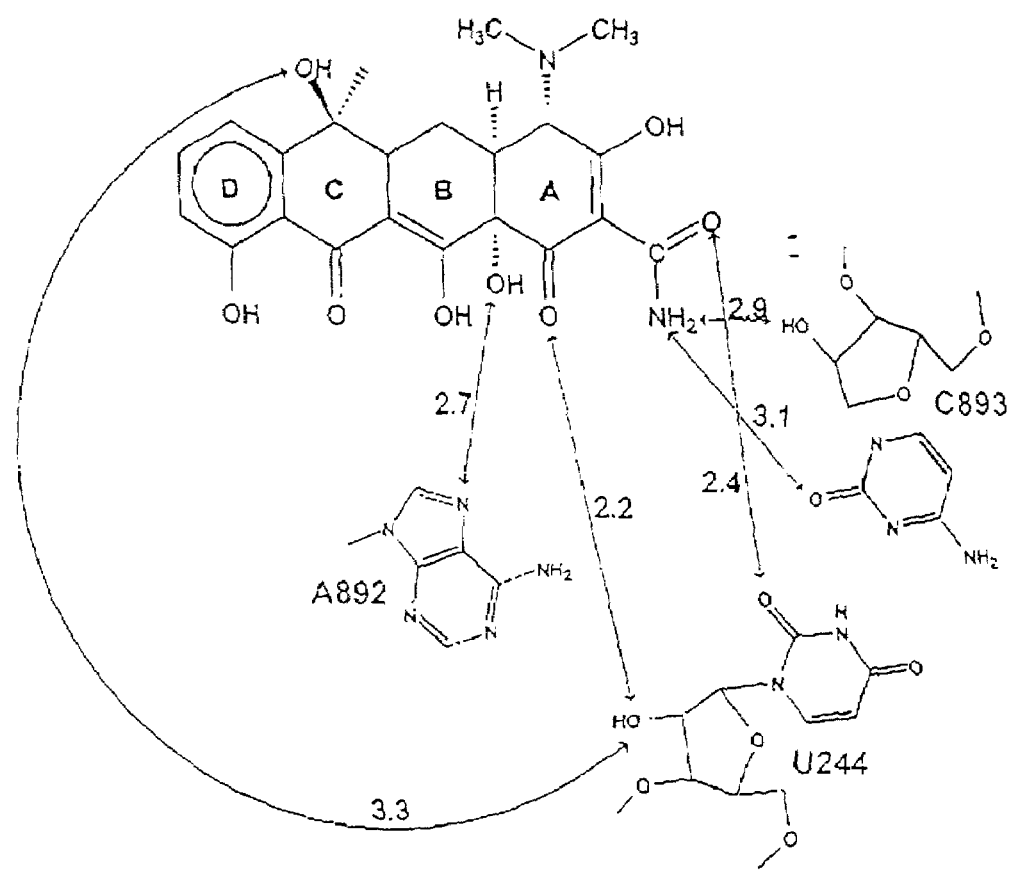
FIG. 4B shows the binding of tetracycline (secondary site) to the 30S ribosome.

Unlike paromomycin, which can bind to an isolated fragment of ribosomal RNA, streptomycin is tightly bound to the phosphate backbone of 16S RNA from 4 different parts of the molecule via both salt links and hydrogen bonds (FIG. 3). It also makes contact with a lysine (K45) from ribosomal protein S12. The four regions of 16S RNA (1490, 915, 526, and 13) had all been implicated in streptomycin binding on the basis of protection [22], crosslinking [25] and mutagenesis data [26–28] (reviewed in [29]).

It has been proposed that translational fidelity involves a switch between two states of the ribosome, an error prone or ram (885) state, characterized by nucleotides 910–912 pairing with 885–887, and a restrictive or hyperaccurate (888) state in which 910–912 pair with 888–890 [30].

The structure of the 30S reported here, like that of the 70S ribosome at 7.8 Å [31] is in the 885 pairing configuration, and hence presumably in the ram state. The tight interactions described above suggest that streptomycin preferentially stabilizes this form. The 888 state A site has a low tRNA affinity, while the 885 state has a higher affinity [30, 32]. Therefore, by stabilizing the 885 state streptomycin would be expected to increase initial binding of non-cognate tRNAs. The preferential stabilization of the 885 state would also make the transition to the 888 state more difficult, thereby also affecting proofreading. Thus, the results offer a structural rationale for the observed properties of streptomycin.

This stabilization of the 885 state by streptomycin suggested by the structure can explain much of the genetic data on the antibiotic. Mutations in S12 lead to a hyper-accurate phenotype [32–38](reviewed by [39]). A weak phenotype manifests itself as streptomycin resistance, where as a strong phenotype (often the result of multiple mutations) leads to streptomycin dependence. Most of these mutants are to varying degrees more hyperaccurate and slower than wild type ribosomes, consistent with destabilization of the 885 state with respect to the 888 state.

All the mutations in S12 map to the a protein loops that connect and hold in place the 908–915 and 524–527 regions, with the exception of one mutant K56 (*E. coli* K53) which contacts H44 (FIG. 3). Thus, S12 stabilizes the same region that is stabilized by streptomycin. In the resistance mutations, the 885 state is destabilized sufficiently so that the additional stabilization induced by streptomycin does not trap the ribosome in this state. In the streptomycin dependent mutants, the 885 state is so destabilized that the 888 (hyper-accurate) form predominates and protein synthesis becomes very slow. Streptomycin can then help stabilize the 885 state sufficiently to restore the balance between the two states and help restore translation.

The K45R (*E. coli* K42) mutation is resistant to streptomycin but is not hyperaccurate [39]. K45 forms a salt bridge with phosphate A913 and thus contributes to stabilization of the 885 state. It also makes direct hydrogen bonding contacts to two OH groups on streptomycin (FIG. 3). Mutation of this lysine to arginine, would disrupt the hydrogen bonding and thereby reduce the affinity of the 30S for streptomycin, leading to resistance. However, the mutation would leave the salt bridge intact, so that the 885 form is not destabilized and thus translation remains normal.

A number of mutations in rRNA also lead to hyperaccuracy [26, 27, 40–43]. Some of these nucleotides are involved in hydrogen bonding interactions in regions close to the streptomycin binding site. Thus, the mutations disrupt interactions that help to stabilize the 885 state. Others such as A915 make no contacts with any other bases. It is possible that mutation of this base leads to more favourable contacts in the 888 state, thus acting by stabilizing the 888 state rather than destabilizing the 885 state.

The ram mutations lead to error-prone ribosomes and are generally found as suppressors of streptomycin resistance. These mutations in S4 [35, 44, 45] and S5 [12] can counter the effect of hyperaccurate mutations in S12 (reviewed by [39]). All ram mutants in S4 and S5 map near the interface between the two proteins with the exception of S52 (*E. coli* S49) which makes a direct hydrogen bond to the backbone of rRNA. At lower resolution [9], it appeared that the ram mutations destablized the S4–S5 interface. However, at atomic resolution, two of the mutations V56 (*E. coli* V53) in S4 and G99 (*E. coli* G103) in S5 are not in contact with the other protein, and it is not obvious from the structure how they would affect stability of the ram state. In fact, there is a cleft between the two proteins which could close up on the 885–888 transition. This leads us to suggest that these residues (and perhaps the corresponding surfaces of S4 and S5) are involved in intimate contacts in the 888 state, and these contacts would be disrupted by the ram mutations. In this model, ram mutations act by destabilizing the 888 state, and thus, shifting the equilibrium to the error prone 885 state. The observation that ram mutations increase the affinity of ribosomes for streptomycin [46] is consistent with this model, since the ribosome would be preferentially in the 885 form. A definitive test of this model must await an atomic resolution structure of the 888 form. Nevertheless, these results provide a structural basis for the notion that a delicate balance exists between the 885 and 888 states for optimal translation, and also explains how disruption of this balance leads to the various phenotypes observed.

Crystallization of Tetracyclin to the 30S Ribosome

Tetracyclines are antibiotics of broad specificity and have been used since the 1940's against a wide range of both Gram-negative and Gram-positive bacteria [47]. These drugs were the first so-called 'broad-spectrum' antibiotics and have been used extensively in both human and veterinary medicine. However, in later years, the widespread use of tetracyclines has been limited by the emergence of significant microbial resistance to these antibiotics. Tetracyclines bind to the 30S ribosomal subunit [48] where it affects exclusively the binding of aminoacylated tRNA to the A-site [49]. There is no effect on the binding of tRNA to the P-site nor on the fidelity of translation [50]. Consistent with the inhibition of tRNA binding to the A-site during translation, tetracycline also prevents binding of both release factors RF-1 and 2 during termination, regardless of the stop codon [51]. In contrast to most antibiotics, resistance to tetracycline is usually not caused by mutations in 16S RNA or ribosomal proteins, but by the presence of several external protein factors which apparently mimic the structure and function of the elongation factors [52–54].

The crystal structure of tetracycline, or 4-(dimethylamino)-1,4,4a,5,5a,6,11,12a-octahydro-3,6,10,12,12a-pentahydroxy-6-methyl-1,11-dioxo-2-naphtacenecarboxamide, in complex with the 30S ribosomal subunit was determined at 3.0 Å resolution. 30S crystals were prepared as described in example 1 above and soaked post crystallization in 80 μM tetracycline. X-ray diffraction data were collected at beamline ID14-4 at the European Synchrotron Radiation Facility in Grenoble, France. The location of the antibiotic within the 30S subunit was identified from difference Fourier maps calculated after a few rounds of maximum-likelihood based refinement of the native 30S structure against the measured structure factor amplitudes.

Two strong binding sites for tetracycline were found within the 30S subunit, one located near the acceptor site for aminoacylated tRNA (the A-site) between the head and the body and another which is present at the interface between three domains in the body of the subunit. The discovery of more binding sites is not surprising, since tetracycline is known to have one primary binding site on the 30S in addition to multiple secondary sites on both subunits [55]. In its primary binding site within the 30S, tetracycline binds exclusively to the 3' major domain in the upper part of the crevice between the head of the 30S and the shoulder and right above the small gap between the stem-loop of H18 of the 5' domain and the long H44 of the 3' minor domain that constitutes the binding site for aminoacylated tRNA. The molecule fits into a small pocket created by residues in H34 that deviate from the canonical A-form RNA double helical conformation in combination with a part of the small H31 stem-loop structure. The contacts to H31 are quite tenuous, however, and the binding of the antibiotic to 16S RNA seems to depend almost exclusively on the interaction with H34. In contrast to what has been proposed earlier, there are no proteins involved in the primary binding of tetracycline. The second binding site of tetracycline seen in the difference maps (although perhaps not as clearly as the primary binding site), is located in the body of the subunit, in close proximity to the penultimate H44 and sandwiched between the functionally important H27 in the central domain and the very top of H11 in the 5' domain of 16S RNA. The binding site it confined on one side by a major groove of H27 (residues 891–894:908–911) and the edge of the curved H11 (residues 242–245). The bulged-out base U244, which reaches across and makes a non Watson-Crick bases pair with C893 in H27 forms the bottom of the binding site. Again, all interaction between the antibiotic and the ribosome is mediated by the RNA, however, the long N-terminal extension of S12 comes very close to the tetracycline (~8 A, Arg19). The binding pocket is approximately 14 A wide and 7 A deep.

Crystallization of Pactamycin to the 30S Ribosome

Pactamycin was isolated from *S. pactum* as a potential new human antitumor antibiotic and is a potent inhibitor of translation in both eukaryotes and prokaryotes [56]. It is believed to inhibit the initiation process, i.e. the initiation factor mediated binding of fMet-tRNA to the ribosome [57], by sequestering the initiation complex in the A-site [58]. This effectively prevents the formation of entire 70S ribosomes and thus halts the translation. The effect upon binding is similar for prokaryotes and eukaryotes [59].

The crystal structure of pactamycin, or 2-hydroxy-6-methylbenzoic acid [5-[(3-acetylphenyl)amino]-4-amino-3-[[(dimethylamino)-carbonyl]amino]-1,2-dihydroxy-3-(1-hydroxyethyl)-2-methylcyclopentyl]methyl ester, in complex with the 30S ribosomal subunit was determined at 3.1 Å resolution. 30S crystals were prepared as described above and soaked post crystallisation in 80 µM pactamycin. X-ray diffraction data were collected at beamline ID14-4 at the European Synchrotron Radiation Facility in Grenoble, France. The location of the antibiotic within the 30S subunit was identified from difference Fourier maps calculated after a few rounds of maximum-likelihood based refinement of the native 30S structure against the measured structure factor amplitudes.

Figure 5:
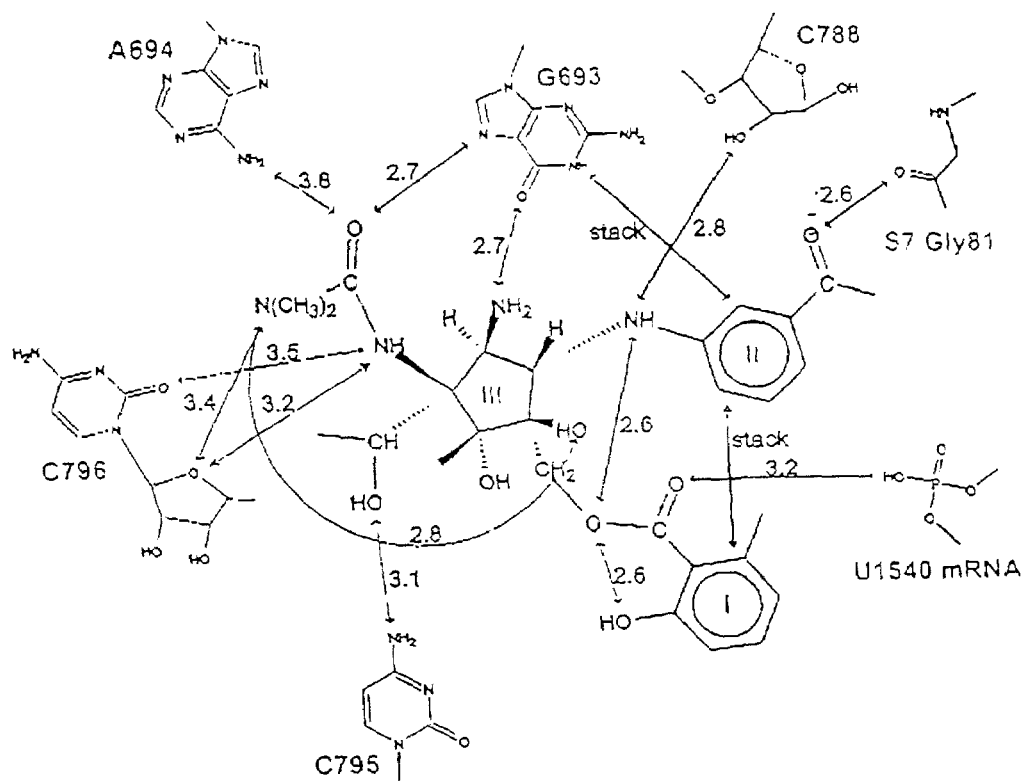
FIG. 5 shows the binding of pactamycin to the 30S ribosome.
Figure 6:
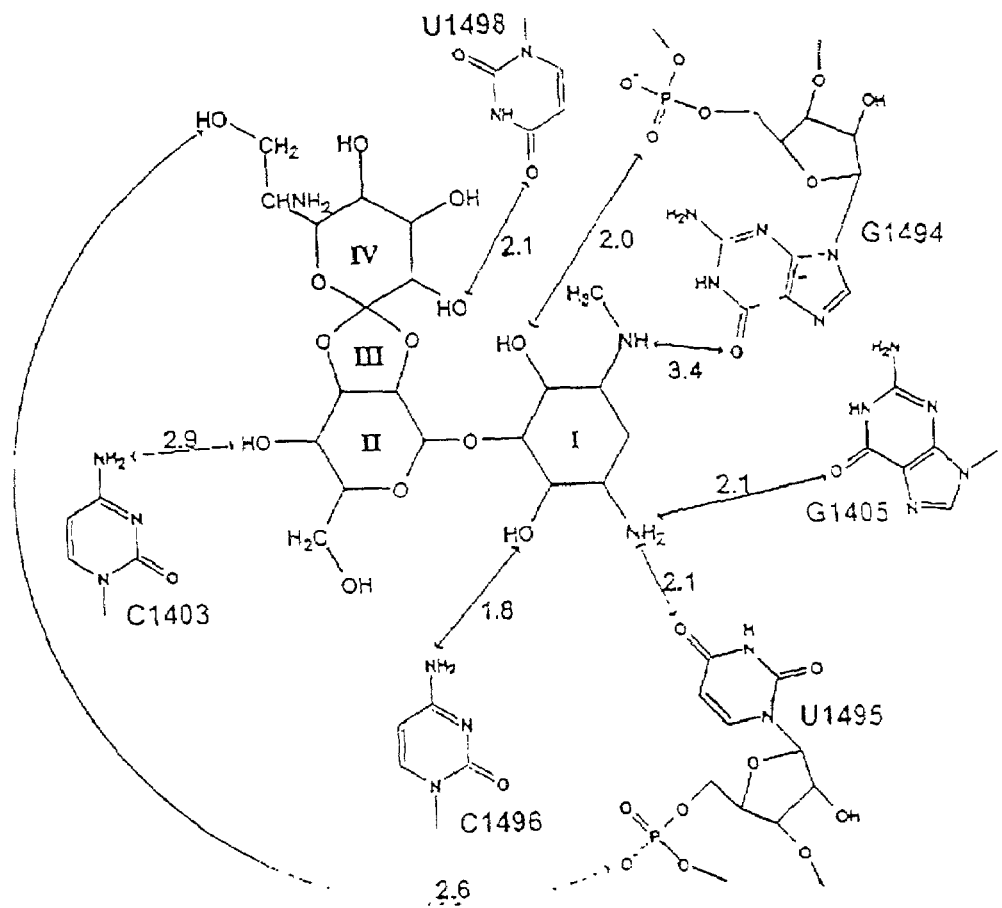
FIG. 6 shows the binding of hygromycin B to the 30S ribosome.

Pactamycin binds to the upper part of the platform, very close to the cleft in the subunit that is responsible for binding of the three tRNA molecules. Only a single strong binding site of pactamycin in the 30S was found. The antibiotic interacts primarily with residues at the apices of the H23b stem loop in the central domain of 16S RNA in addition to a couple of bases from the nearby H24a (FIG. 5). The site of binding is very close to the 3' minor domain and the ultimate H45, but there is not direct interaction with this region. In its binding to the RNA, pactamycin extends the stacking of bases in the tetra loop of H23b and mimics RNA both with respect to the bases and the sugar phosphate backbone. In this region, the H24a loop forms a regular helical stem loop to which the H23b stem loop is attached with interactions mainly between bulging bases in H23b and the backbone of H24a. The bases near the apices of H23b curve around and pack into the major groove of H24b, and this trend is extended by two "bases" by a single pactamycin molecule. The antibiotic folds up so that the two distal 6-carbon rings are stacked against each other like nucleotides with the 5-carbon in between resembling a sugar ring. The $NCON(CH_3)_2$ extension on the central ring even to some extent mimics the phosphate ester moiety of RNA. The nearest proteins are S7 and S11, and there appears to be a weak hydrogen bond to the backbone carbonyl of Gly81 of S7.

In FIG. 5 an interaction with a residue "U1450 mRNA" is indicated. From the data this residue is not continuous with the main 16S RNA sequence, but appears as part of a stretch of mRNA which appears in the crystal. However, it is believed that it represents the very end (3' end) of 16S RNA, based on sequence, thus it has been given sequence numbers from the 16S in this figure (1539–1544). However, in the table of coordinates, these residues have been separately numbered 1–6, the coordinates being shown immediately following those of the 16S RNA.

Even though pactamycin has been described as binding primarily to the ribosomal P-site [57, 60], the observed protections for this antibiotic can be regarded as pertaining rather to the E-site. This notion is in more agreement with the present structure, in which the two "bases" of pactamycin coincide with the two last bases of the E-site codon of mRNA as observed in the native 30S structure [61]. In fact, pactamycin together with the first base in the E-site codon of the native structure form a triplet codon mimic in approximately the right position for interaction with an E-site tRNA. However, in the antibiotic bound structure, the actual position of the bases in the E-site codon is shifted remarkably, in a way that precludes a possible interaction with an E-site bound tRNA. In the native 30S structure, a kink is observed in the backbone of the messenger RNA at the interface between the P- and E-sites, however, the overall path of the mRNA is still relatively straight and leads between the long 73–90 beta hairpin of S7 and the stem loops of H23 and H24a of the platform. In the pactamycin-bound structure, however, the mRNA in the E-site is pushed towards the back of the subunit, and in between H28 of the head and the hairpin of S7. This is a remarkable distortion that comprises on average 12.5 A for the last of the bases in the E-site codon.

Crystallization of Hygromycin B to the 30S Ribosome

Hygromycin B is a monosubstituted 2-deoxystreptamine-containing aminoglycoside antibiotic originally isolated as a secondary antibiotic substance from *S. hygroscopicus* [62]. It is an unusual aminoglycoside antibiotic in that it is active against both prokaryotic and eukaryotic cells and differs in structure from other aminoglycosides [63]. The drug works primarily by inhibiting the translocation step of elongation [63–65] and to a lesser extent causes misreading of messenger RNA [50, 65]. The antibiotic affects EF-2 (EF-G) mediated translocation of A-site bound tRNA to the P-site in eukaryotes, but does not affect either binding of the factor to the ribosome or the hydrolysis of the bound GTP, a process that has been shown to be separate from translocation [63]. The inhibition of translocation is accompanied by an increase in the affinity of the A-site for aminoacylated tRNA [50].

The crystal structure of hygromycin B, or O-6-amino-6-deoxy-L-glycero-D-galacto-heptopyranosylidene-(1→2–3)-O-β-D-talopyranosyl-(1→5)-2-deoxy-$N^3$-methyl-D-streptamine, in complex with the 30S ribosomal subunit was determined at 3.1 A resolution. 30S crystals were prepared as described above, and soaked post crystallization in 80 µM hygromycin. X-ray diffraction data were collected at beamline ID14-4 at the European Synchrotron Radiation Facility in Grenoble, France. The location of the antibiotic within the 30S subunit was identified from difference Fourier maps calculated after a few rounds of maximum-likelihood based refinement of the native 30S structure against the measured structure factor amplitudes.

Hygromycin B has a single clear binding site within the 30S consistent with the finding that it has a monophasic effect on translation [66]. It binds close to the very top of the long, penultimate helix 44 of 16S RNA, in a region that contains the A-, P-, and E-site tRNA binding sites. The antibiotic is in contact only with 16S RNA (not any proteins), and only with helix 44. In fact, it is located in the major groove of the helix, very close to the helical axis, and thus surrounded by residues from both RNA strands in the region 1490–1500 and 1400–1410. Hygromycin B almost exclusively contacts the bases, as opposed to the backbone, of RNA, and would on this basis be expected to be highly sequence-specific. The nearest protein is S12, which is known to be important in decoding, but is more than 14 Å away from the hygromycin binding site. Binding of hygromycin B does not seem to induce any significant alterations in the structure of RNA, and appears to be governed by strong base-specific hydrogen-bonds spanning more than three sequential bases in one strand of helix 44. This is possible because the structure of the three-ring antibiotic is unfolded in its binding site within the 30S and thus makes the molecule about 13 Å long.

Hygromycin B binds to the 30S in an important functional region which is also the target for other antibiotics such as paromomycin and gentamycin. Both these antibiotics bind further down helix 44 than does hygromycin and thus affect adenosines A1492 and A1493 which have been implicated as crucial in decoding. Interestingly, Ring II of paromomycin, which is also found in other aminoglycoside antibiotics including gentamycin, adopts an almost identical orientation as Ring I of hygromycin, only about 3 Å further down the helix, or exactly what corresponds to one residue. This indicates that this type of six-ring is an important general means of antibiotic binding, since abolishment of the interaction with RNA (in the case of hygromycin) leads to resistance [67, 68].

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

EXAMPLES

Example 1

Generation of Crystals of the 30S Ribosomal Subunit Bound to Antibiotics

Crystallization of the 30S Ribosomal Subunit

Crystals of *T. thermophilis* 30S ribosomal subunits were obtained by an optimization of the procedure reported by Trakhanov et al. (Trakhanov, S. D. et al *FEBS Lett.* 220, 319±322 (1987)) with respect to pH and concentrations of $Mg^{2+}$ ions and 2-methyl-2,4-pentanediol (MPD) as described in Wimberly et al. *Nature* 407, 327–339 (2000). The final conditions were 250 mM KCl, 75 mM $NH_4Cl$, 25 mM $MgCl_2$ and 6 mM 2-mercaptoethanol in 0.1 M potassium caco-dylate or 0.1 M MES (2-N-morpholino-ethanesulphonic acid) at pH 6.5 with 13±17% MPD as the precipitant. 30S crystals completely lacked ribosomal protein S1. Selective removal of the S1 subunit prior to crystallization improved both the crystal size and reproducibility in crystal growth. Typical procedures used to remove the S1 subunit include the use of poly-U sepharose chromatography followed by extensive salt washing as described by Subramanianet et al. *Eur. J. Biochem.* 119, 245–249 and Subramanian, A. R., (1983) In Progress in Nucleic Acid Research and Molecular Biology, v. 28, W. E. Cohn, (ed.) 101–142. *Academic Press,* New York, p.104. 30S crystals typically reached a maximum size in about 6 weeks at 4° C. The largest crystals, which were required for high-resolution data collection, grew to a size of 80±100×80±100×200±300 μm.

Generation of 30S Crystals Bound to Antibiotics

X-ray diffraction data were collected from multiple crystals of *Thermus thermophilus* 30S subunits soaked with antibiotics post-crystallization at a concentration at which the antibiotics were known to block translation in vivo as described in Ditlev et al. *Cell* (2000) 103, 1143–1154. For example, large, single 30S crystals were soaked in 80 μM of either tetracycline (4-[dimethylamino]-1,4,4a,5,5a,6,11,12a-octahydro-3,6,10,12,12a-pentahydroxy-6-methyl-1,11-di-oxo-2-naphtacenecarboxamide, obtained from ICN), pactamycin (2-hydroxy-6-methylbenzoic acid [5-[(3-acetylphenyl)amino]-4-amino-3-[[(dimethylamino)-carbonyl]amino]-1,2-dihydroxy-3-(1-hydroxy-ethyl)-2-methylcyclopentyl]methyl ester, obtained from the U.S. National Cancer Institute, Bethesda, Md.), or hygromycin B (O-6-amino-6-deoxy-L-glycero-D-galacto-heptopyranosylidene-(12-3)-O-D-talopyranosyl-(15)-2-deoxy-N3-methyl-D-streptamine, obtained from ICN) before flash-freezing in liquid N2. For comparison, the minimum inhibitory concentrations of these antibiotics is 0.3–3 μM for tetracycline (Ross et al. (1998) Antimicrob. Agents Chemother. 42, 1702–1705), 8–80 μM for pactamycin (Cohen et al. (1969) *Biochemistry* 8, 1327–1335), and around 6 μM for hygromycin B (Cabanas et al. (1978) *Eur. J. Biochem.* 87, 21–27).

Example 2

Computer Based Method of Rational Drug Design

This example provides a computer based method of rational drug design. To obtain structural information about the protein/drug interaction to allow rational drug design, it is first necessary to prepare a crystal of the complex, the complex being the drug bound to the 30S ribosomal subunit. A crystal of the complex can be produced using two different methods. In a first method, the actual complex itself is crystallized using the prescribed conditions set forth for the native 30S ribosomal subunit. Once crystals of a suitable size have grown, x-ray diffraction data are collected and analyzed as described by Greer et al., *J. of Medicinal Chemistry,* Vol. 37, (1994), 1035–1054. This process usually involves the measurement of many tens of thousands of diffracted x-rays over a period of one to several days depending on the crystal form and the resolution of the data required. According to the method, crystals are bombarded with x-rays. The crystals diffract the rays, creating a geometrically precise splatter of spots on photographic film or electronic detectors. The distribution of atoms within the crystal influences the pattern of spots. Subtraction of the data, F.sub.ligand-F.sub.native, using phases from the atomic model of the 30S ribosomal subunit structure produces the electron density of only the drug molecule. Visualization of the observed electron density superimposed on the atomic coordinates derived from the same crystal form provides a determination of key protein drug interactions that are necessary for rational drug design. In the normal practice of the invention, this would be an iterative process involving several cycles of modelling with each of the new drugs synthesized as a result of the changes suggested by the crystal structure of the complex. In the second commonly practiced method, the drugs or ligands may be soaked into the crystal because of the inherently large aqueous solvent channels present in protein crystals. (See, e.g., Carter et al., 244 *Science*, 1195–1198 (1989). The crystalline complex thus formed follows the same procedure described above to provide the electron density of the drug of interest. Recent advances in rational drug design are described in Gane, P. J. and Dean, P. M. Curr.Op.Struct.Biol. (2000) 10:4:401–404.

Example 3

An Example of a Computer Based Method for Identifying a Potential Inhibitor of the 30S Ribosome This example discloses a computer based method to identify a potential inhibitor of the 30S ribosome. The structure of an antibiotic bound to the 30S defines "crystallographically known sites". A number of molecular docking procedures can be used to design novel binders that also bind to these sites. For example, the programs MCSS and Ludi can be used to dock small fragments that can then be linked together to form a novel ligand. Molecular docking procedures, as used herein, refer to the use of computer programs, as defined herein, to identify potential ligands that are predicted to stably interact with a defined site on the 30S ribosome subunit. Alternatively, libraries of compounds as described herein are converted into 3D format using programs such as Concord (Tripos), CeriusII (Accelrys) etc. The 3D structures of the ligands are then docked against a site on the ribosome. This site can be a confirmed site (i.e. one where there is crystallographic or other evidence of binding of a known molecule) or a novel site. Docking methods typically involve using computer programs DOCK (UCSF), FleXX(Tripos), Ludi(Accelrys), Gold(CCDC, Cambridge, UK). The docking of a compound library results in a "ranking" of the molecules. An energy threshold based on their predicted interaction energy or score. It is possible to choose a "minimum score" and select compounds that are predicted to score better than this minimum value (threshold). This energy theshold is then used to select virtual hits. For example, any ligand that scores better than an arbitrary value –20 would be selected as a hit. Another example would be to select the best scoring 1000 compounds as hits. The selected hits can then be acquired through the companies that supply the compounds (and the catalogues). These compounds are then screened experimentally to identify the "real" hits, i.e. the molecules that are active, as defined herein.

This approach can be extended to those sites where only indirect evidence of functional importance is available, such as results of foot-printing of known antibiotics, 30S mutational data etc. Indeed, the 30S structure in the presence or absence of bound antibiotic can be used for the de-novo search of novel binders using docking methods described above.

Example 4

How to Determine the Structure of 30S from a Species that is not *Thermophilus*

This example describes how 'molecular replacement' of the known three dimensional structure of the 30S ribosomal subunit of *Thermus thermophilis* can be used to facilitate the structure determination of other 30S ribosomal subunits from non *T. thermophilus* prokaryotes, as defined herein, in particular those that are pathogenic to humans. Molecular replacement, as the name suggests, uses a molecule having a known structure, in this case, the 30S ribosomal subunit of *T. thermophilus*, as a starting point to model the structure of the unknown crystalline sample. This technique is based on the principle that two molecules that have similar structures and similar orientations and positions in the unit cell diffract similarly. Effective use of this technique requires that the structures of the known and unknown molecules be highly homologous. Computer programs used in molecular replacement analyses are AMORE (part of the CCP4 suite; J.Navaza, Acta Cryst. A50, 157–163 (1994)), CNS(X) (Brunger, A. T., Adams, P. D., Clore, G. M., DeLano, W. L., Gros, P., Grosse-Kunstleve, R. W., Jiang, J.-S., Kuszewski, J., Nilges, N., Pannu, N. S., Read, R. J., Rice, L. M., Simonson, T., and Warren, G. L. (1998), Crystallography and NMR system (CNS): A new software system for macromolecular structure determination, Acta Cryst. D54, 905–921); EPMR (Charles R. Kissinger, Daniel K. Gehlhaar & David B. Fogel, "Rapid Automated Molecular Replacement by Evolutionary Search", Acta Crystallographica, Section D, 1999 February;55 (Pt 2):484–91; REPLACE (L. Tong J. Appl. Cryst. 26, 748–751, (1993); L. Tong & M. G. Rossmann Acta Cryst. A46, 783–792, (1990)); and MOLREP (A.Vagin, A.Teplyakov, MOLREP: an automated program for molecular replacement., J. Appl. Cryst. (1997) 30, 1022–1025).

In brief, 'molecular replacement' involves positioning the known structure in the unit cell in the same location and orientation as the unknown structure. Once positioned, the atoms of the known structure in the unit cell are used in the so-called Structure Factor Equation to calculate the structure factors that would result from a hypothetical diffraction experiment. The Structure Factor Equation takes the form:

$$F_H = \sum_{j=1}^{N} f_j \exp 2\pi i (hx_j + ky_j + lz_j),$$

where F(H) is the structure factor of the molecule at the point (H=hkl) on the detector surface, $f_j$ is the atomic structure factor (that is, it represents the scattering properties of the individual atom), N is the number of non-hydrogen atoms, and $x_j$, $y_j$, $z_j$ are the fractional coordinates of atom j in the unit cell. The structure factor calculated is generally a complex number containing both the amplitude and phase data for the molecular replacement model at each point (hkl) on the detector surface. These phases can then be refined using CNS or other refinement programs to produce even better phases. Finally, the new structure can be built into the density from these phases and the measured amplitudes and then refined to get an accurate structure of the new molecule. These calculated phases are used, in turn, with the experimental amplitudes measured for the unknown structure to calculate an approximate electron distribution. "Refinement" refers to the repeated use of programs such as CNS and involves the computation of rigid body, conjugate gradient minimisation, simulated annealing and conjugate gradient minimisation. The calculated electron density is then inspected and the model is altered by hand or computationally, followed by further rounds of refinement. In this manner, the approximate structure can be fine-tuned to yield a more accurate and often higher resolution structure.

The molecular replacement technique requires knowledge of the number of molecules, and the orientation and position of each molecule within the unit cell as defined herein. Initially, the electron density calculated from the phases from the molecular replacement model and experimental amplitudes closely resembles the electron density of the model. Only after refinement of the initial structure, as described herein, will the success or failure of the method be apparent. For instance, failure occurs if the initial structure fails to converge (as represented by a correlation value) or if the refined structure diverges from the structure of the model during the refinement process. In cases where the unknown structure is a ligand bound to a 30S ribosomal subunit, molecular replacement's success is evident when the result is a structure whose only difference is added electron density that represents the ligand-bound 30S subunit. The determination of such structures is important in the area of pharmaceutical drug testing where the structure of 30S subunit-bound drugs and intermediates yield important information about binding and mechanism. Similarly, new mutants of the 30S subunit or variations of 30S subunit bound inhibitors are well suited for molecular replacement, as are structures of the same molecule that have crystallized in different symmetry groups.

Example 5

A Method of Modelling a Structure of the 30S Ribosomal Subunit Bound to a Modulator This example describes how to model a structure of the 30S ribosomal subunit bound to a modulator. Potential modulators of 30S ribosomal function are examined by computer modeling using docking programs such as GRAM, DOCK, or AUTODOCK [Dunbrack et al., Folding & Design, 2:27–42 (1997)] and the known three dimensional structure of the 30S ribosomal subunit. This procedure can include computer fitting of these potential modulators to ascertain how well the shape and the chemical structure of the potential modulator will bind to the 30S subunit. Computer programs are also employed to estimate the attraction, repulsion, and steric hindrance of the 30S subunit with a modulator/inhibitor.

Example 6

Methods of Designing a Molecule that Interacts with the 30S Ribosomal Subunit

This example describes methods for designing potential drugs that bind specifically to the 30S ribosomal subunit. From the analysis of the structure of the 30S ribosomal subunit in complex with antibiotics, a person skilled in the art will identify the key interactions between the known antibiotic and the 30 S subunit. The spatial arrangements of these interactions identify potential features that a molecule may possess to interact with the 30S. Examples of these features are: hydrogen bond donor, HB acceptor, hydrophobic, aromatic, positively ionisable, negatively ionisable, positive charge, negative charge etc. . . . The relative spatial arrangement of these features (i.e. distances separating each pair of features, angles etc.) defines a set of pharmacophores. Pharmacophores can also be used for the de-novo design of molecules that fulfil the features of the pharmacophore. Computer programs, such as Catalyst (Accelrys) and Unity (Tripos) that generate the parameters defining a pharmacophore, can be used to search large databases of compounds for potential binding partners of the 30S ribosomal subunit. Commonly used databases include the Available Chemical Directory (ACD) from MDL as well as various electronic catalogues of publicly available compounds such as the National Cancer Institute (NCI, US) catalogue, ComGenex catalogue (Budapest, Hungary), Asinex (Moscow, Russia) etc.

For example, the analysis of the interaction between tetracycline and the 30S ribosome shows that only one edge of the tetracycline molecule interacts with the RNA. Furthermore, that edge is composed of a hydoxyl-carbonyl-hydroxyl that potentially interacts with a $Mg^{2+}$ ion present in the binding site. Compound databases are searched for any molecule that displays aligned hydrogen bond donor—hydrogen bond acceptor—hydrogen bond donor, or preferentially hydroxyl-carbonyl-hydroxyl (angle 180+/−10 deg), separated by 2.6 A +/−0.5 A (the pharmacophore). All molecules that fulfil these criteria are identified as potential binders that could be tested in a binding partner assays described herein.

Analysis of the structure of the antibiotics in complex with the 30S ribosomal subunit also enables those skilled in the art to design novel binders by combining 2 or more fragments of interacting molecules. For example, novel molecules may be designed by combining all or parts of paromomycin and streptomycin.

The activity of all molecules designed above can be tested using the described assays.

Example 7

Determination of the Activity of a Binding Partner of the 30S

This example describes functional assays used to determine the activity of a potential binding partner of the 30S ribosomal subunit. Typically these assays include either cell free translation assays or analysis of the 'partial reactions' such as tRNA or mRNA binding that are required for polypeptide chain synthesis.

A. In vitro Translation.

The ribosome is a molecular machine that makes proteins. A 30S binding partner, useful according to the invention, can inhibit translation. To identify the functional activity of a 30S binding partner, a translational assay can be used as described in Zubay G In vitro synthesis of protein in microbial systems. Annu Rev Genet 1973;7:267–87 in the presence or absence of a putative 30S ribosomal subunit binding partner. A molecule that increases or decreases translation by at least 10% is identified as a binding partner.

B. Partial Reactions.

During protein synthesis, the 30S ribosomal subunit interacts with a large number of ligands—mRNAs, tRNAs, proteins etc. Partial reactions involved in protein synthesis are, therefore, used to demonstrate the inhibition or activation of ribosomal function by a 30S bound compound. There are three main stages of translation—initiation, elongation and termination. Such assays as tRNA binding (as described in Ashraf, S. S., Ansari, G., Guenther, R., Sochacka, E., Malkiewicz, A., Agris, P. F. (1999): The Uridine in "U-turn": Contributions to tRNA-ribosomal Binding. RNA 5, 503–511), and mRNA binding (as described in Von Ahsen, U., Green, R., Schroeder, R., Noller, H. (1997): Identification of 2'hydroxyl Groups Required for Interaction of a tRNA Anticodon Stem-loop Region with the Ribosome. RNA 3:49–56) are performed in he presence or absence of a putative 30S modulator to identify inhibitors or activators that which modulate the function of 30S subunit.tRNA binding and/or MRNA binding

Example 8

A Method of Preparing a Computer Fitting Model of Binding of a Binding Partner of the 30S Subunit and the 30S Subunit Starting with the 3D coordinates of the 30S ribosomal subunit structure, a co-factor or binding partner, such as tRNA, mRNA, or EF-G protein, is manually docked into its binding site based upon biochemical data and making use of standard molecular graphics software packages (such as QUANTA or INSIGHT from Accelrys). The in silico coordinates of the complex thus generated is then refined using energy minimisation algorithms as described elsewhere (under modelling of mutated ribosome). An example of a similar procedure is the modelling of the 70S ribosome structure complexed with ribosomal protein S8 based on high resolution coordinates of the 30S and 50S ribosome structures (Lancaster L, Culver G M, Yusupova G Z, Cate J H, Yusupov M M, Noller H F., (2000) RNA May;6(5): 717–729

Example 9

A Method of Characterizing Binding of a Binding Partner of the 30S Subunit to the 30S Subunit This example describes commonly used methods to characterize potential binding partners of the 30S ribosomal subunit.

A. Binding of Radioactively Labelled Compounds to the 30S Ribosomal Subunit.

This approach was successfully used for the identification of some ribosomal binders, for example, $^3$H-labelled tetracycline, chloramphenicol, oxazolidinones etc. Direct binding of the radioactive compound or the displacement of the known radioactive 30S binding partner (known antibiotics) by different compounds can be used for identification of the potential 30S binder as described in Matassova N. B., Rodnina M. V., Endermann R., Kroll H. P., Pleiss U., Wild H., Wintermeyer W. Ribosomal RNA is the target for oxazolidinones, a novel class of translational inhibitors. RNA. 1999. V.5. P.939–946; Bischof O, Urlaub H, Kruft V, Wittmann-Liebold B Peptide environment of the peptidyl transferase center from *Escherichia coli* 70 S ribosomes as determined by thermoaffinity labeling with dihydrospiramycin. J Biol Chem 1995 Sep. 29;270(39):23060–4 and Bischof O, Kruft V, Wittmann-Liebold B Analysis of the puromycin binding site in the 70 S ribosome of *Escherichia coli* at the peptide level. J Biol Chem 1995 Jul. 15;269(28): 18315–9

B. Fluorescence Techniques—the Binding and Displacement of Fluorescently Labelled Antibiotics to 30S Ribosomal Subunits.

The binding or displacement of fluorescently labelled antibiotics or RNA binding ligands to 30S ribosomal subunits can be measured by a number of fluorescence techniques, including fluorescence anisotropy or polarisation, the enhancement of fluorescence on binding and the quenching of fluorescence on binding.

Polarisation P $P=(I_\parallel-I\perp)/(I_\parallel+I\perp)$

The anisotropy r $r=((I_\parallel-I\perp)/(I_\parallel+2I\perp)$ $I_\parallel$ is the intensity of the emission viewed through parallel polarisers and $I\perp$ is the intensity of the emission viewed through perpendicularly arranged polarisers. In solution fluorescent molecules are generally rotationally free and measured anisotropies are low. On binding, they become rotationally constrained and their anisotropy increases to a maximum value as described in Epe B, Woolley P, Hornig Competition between tetracycline and tRNA at both P and A sites of the ribosome of *Escherichia coli*. FEBS Lett 1987 Mar. 23;213(2):443–7 and Epe B, Woolley P. The binding of 6-demethylchlortetracycline to 70S, 50S and 30S ribosomal particles: a quantitative study by fluorescence anisotropy. EMBO J 1984 January;3(1):121–6

Anisotropy can therefore be used to measure binding of a fluorescently labelled antibiotic or RNA binding ligand to a 30S ribosomal subunit. Fluorescence polarisation can be also used to measure binding of a fluorescently labelled antibiotic or RNA binding ligand to a large RNA molecule or ribonucleoprotein complex.

Example 10

A Method of Analyzing a 30S Ligand Complex

The 30S ligand complex is analysed as described in Barrett J F (2000) Linezolid Pharmacia Corp Curr Opin Investig Drugs 1(2):181–7; Lin A H, Murray R W, Vidmar T J, Marotti K R (1997) Antimicrob Agents Chemother 41(10):2127–31; Epe B, Woolley P, Hornig (1987) FEBS Lett 213(2):443–7 and Epe B, Woolley P. (1984) EMBO J 3(1):121–6

Example 11

A Method of Modelling the Structure of a Mutant 30S Subunit.

The structure of the ribosome is visualised using a standard molecular modelling package such as Insight (Accelrys). Using the graphical tools, it is possible to interact with the 3D coordinates of selected RNA bases or protein side chains and mutate them. The 3D coordinates are then be refined using standard molecular mechanics tools for energy minimisation (such as CHARMM, Insight (Accelrys)). The refined coordinates are then saved in electronic format and used for subsequent drug design work.

Although the foregoing invention has been described in some detail by way of illustration and example for purposes of clarity of understanding, it will be apparent to those skilled in the art that certain changes and modifications may be practised. Therefore, the descriptions and examples should not be construed as limiting the scope of the invention, which is delineated by the appended claims.

REFERENCES

1. Garrett, R. A. et al. (eds.) The Ribosome. Structure, Function, Antibiotics and Cellular Interactions (*ASM Press,* Washington, D.C., 2000).
2. von Böhlen, K. et al. Characterization and preliminary attempts for derivatization of crystals of large ribosomal subunits from Haloarcula marismortui diffracting to 3 Å resolution. *J. Mol. Biol.* 222, 11–15 (1991).
3. Trakhanov, S. D. et al. Crystallization of 70 S ribosomes and 30 S ribosomal subunits from Thermus thermophilus. *FEBS Lett.* 220, 319–322 (1987).
4. Glotz, C. et al. Three-dimensional crystals of ribosomes and their subunits from eu- and archaebacteria. *Biochem. Int.* 15, 953–960 (1987).

5. Yonath, A. et al. Characterization of crystals of small ribosomal subunits. *J. Mol. Biol.* 203, 831–834 (1988).
6. Yusupov, M. M., Tischenko, S. V., Trakhanov, S. D., Ryazantsev, S. N. & Garber, M. B. A new crystalline form of 30 S ribosomal subunits from *Thermus thermophilus*. *FEBS Lett.* 238, 113–115 (1988).
7. Yonath, A. et al. Crystallographic studies on the ribosome, a large macromolecular assembly exhibiting severe nonisomorphism, extreme beam sensitivity and no internal symmetry. *Acta Crystallogr* A54, 945–55 (1998).
8. Tocilj, A. et al. The small ribosomal subunit from *Thermus thermophilus* at 4.5 A resolution: pattern fittings and the identification of a functional site. *Proc Natl Acad Sci USA* 96, 14252–7 (1999).
9. Clemons, W. M., Jr. et al. Structure of a bacterial 30S ribosomal subunit at 5.5 Å resolution. *Nature* 400, 833–840 (1999).
10. Otwinowski, Z. & Minor, W. in *Methods in Enzymology* (eds. Carter, C. W. J. & Sweet, R. M.) 307–25 (Academic Press, New York, 1997).
11. Terwilliger, T. & Berendzen, J. Automated MAD and MIR structure determination. *Acta Cryst* D55, 849–861 (1999).
12. Abrahams, J. P. Bias reduction in phase refinement by modified interference functions: introducing the gamma correction. *Acta Cryst.* D53 (1997).
13. de la Fortelle, E. & Bricogne, G. in *Methods in Enzymology* (eds. Carter, C. W., Jr. & Sweet, R. M.) 472–93 (Academic Press, New York, 1997).
14. Hartmann, R. K. & Erdmann, V. A. *Thermus thermophilus* 16S rRNA is transcribed from an isolated transcription unit. J Bacteriol 171, 2933–41 (1989).
15. Cowtan, K. & Main, P. Miscellaneous algorithms for density modification. *Acta Crystallogr D Biol Crystallogr* 54, 487–93 (1998).
16. Jones, T. A. & Kjeldgaard, M. Electron-density map interpretation. *Meth. Enzymol.* 277B, 173–207 (1997).
17. Brünger, A. T. et al. Crystallography & NMR system: A new software suite for macromolecular structure determination. *Acta Crystallogr D Biol Crystallogr* 54, 905–21 (1998).
18. Choli, T., Franceschi, F., Yonath, A. & Wittmann-Liebold, B. Isolation and characterization of a new ribosomal protein from the thermophilic eubacteria, *Thermus thermophilus, T. aquaticus* and *T. flavus. Biol Chem* Hoppe Seyler 374, 377–83 (1993).
19. Mueller, F. & Brimacombe, R. A new model for the three-dimensional folding of *Escherichia coli* 16 S ribosomal RNA. I. Fitting the RNA to a 3D electron microscopic map at 20 A. *J Mol Biol* 271, 524–44 (1997).
20. Fourmy, D., Recht, M. I., Blanchard, S. C. & Puglisi, J. D. Structure of the A site of *Escherichia coli* 16S ribosomal RNA complexed with an aminoglycoside antibiotic. *Science* 274, 1367–71 (1996).
21. Yoshizawa, S., Fourmy, D. & Puglisi, J. D. Recognition of the codon-anticodon helix by ribosomal RNA. *Science* 285, 1722–5 (1999).
22. Moazed, D. & Noller, H. F. Interaction of antibiotics with functional sites in 16S ribosomal RNA. *Nature* 327, 389–394 (1987).
23. Brink, M. F., Brink, G., Verbeet, M. P. & de Boer, H. A. Spectinomycin interacts specifically with the residues G1064 and C1192 in 16S rRNA, thereby potentially freezing this molecule into an inactive conformation. *Nucleic Acids Res* 22, 325–31 (1994).
24. Wittmann-Liebold, B. & Greuer, B. The primary structure of protein S5 from the small subunit of the *Escherichia coli* ribosome. FEBS Lett 95, 91–8 (1978).
25. Gravel, M., Melancon, P. & Brakier-Gingras, L. Crosslinking of streptomycin to the 16S ribosomal RNA of *Escherichia coli*. Biochemistry 26, 6227–32 (1987).
26. Montandon, P. E., Wagner, R. & Stutz, E. *E. coli* ribosomes with a C912 to U base change in the 16S rRNA are streptomycin resistant. *Embo J* 5, 3705–8 (1986).
27. Pinard, R., Payant, C., Melancon, P. & Brakier-Gingras, L. The 5' proximal helix of 16S rRNA is involved in the binding of streptomycin to the ribosome. *Faseb J* 7, 173–6 (1993).
28. Melancon, P., Lemieux, C. & Brakier-Gingras, L. A mutation in the 530 loop of *Escherichia coli* 16S ribosomal RNA causes resistance to streptomycin. *Nucleic Acids Res* 16, 9631–9 (1988).
29. Spahn, C. M. & Prescott, C. D. Throwing a spanner in the works: antibiotics and the translation apparatus. *J Mol Med* 74, 423–39 (1996).
30. Lodmell, J. S. & Dahlberg, A. E. A conformational switch in *Escherichia coli* 16S ribosomal RNA during decoding of messenger RNA. *Science* 277, 1262–7 (1997).
31. Cate, J. H., Yusupov, M. M., Yusupova, G. Z., Earnest, T. N. & Noller, H. F. X-ray crystal structures of 70S ribosome functional complexes [see comments]. *Science* 285, 2095–104 (1999).
32. Pape, T., Wintermeyer, W. & Rodnina, M. V. Conformational switch in the decoding region of 16S rRNA during aminoacyl-tRNA selection on the ribosome. *Nat Struct Biol* 7, 104–7 (2000).
33. Funatsu, G. & Wittmann, H. G. Ribosomal proteins. 33. Location of amino-acid replacements in protein S12 isolated from *Escherichia coli* mutants resistant to streptomycin. *J Mol Biol* 68, 547–50 (1972).
34. Ito, T. & Wittmann, H. G. Amino acid replacements in proteins S5 and S12 of two *Escherichia coli* revertants from streptomycin dependence to independence. *Mol Gen Genet* 127, 19–32 (1973).
35. van Acken, U. Proteinchemical studies on ribosomal proteins S4 and S12 from ram (ribosomal ambiguity) mutants of *Escherichia coli*. *Mol Gen Genet* 140, 61–8 (1975).
36. Timms, A. R. & Bridges, B. A. Double, independent mutational events in the rpsL gene of *Escherichia coli*: an example of hypermutability? *Mol Microbiol* 9, 335–42 (1993).
37. Timms, A. R., Steingrimsdottir, H., Lehmann, A. R. & Bridges, B. A. Mutant sequences in the rpsL gene of *Escherichia coli* B/r: mechanistic implications for spontaneous and ultraviolet light mutagenesis. *Mol Gen Genet* 232, 89–96 (1992).
38. Tubulekas, I., Buckingham, R. H. & Hughes, D. Mutant ribosomes can generate dominant kirromycin resistance. *J Bacteriol* 173, 3635–43 (1991).
39. Kurland, C. G., Hughes, D., Ehrenberg, M. Limitations of translational accuracy. (ed. Neidhardt, F. C., Curtiss, III, R., Ingraham, J. L., Lin, E. C. C., Low, K. B., Magasanik, B., et al) (*American Society for Microbiology Press,* Washington, D.C., 1996).
40. Montandon, P. E., Nicolas, P., Schurmann, P. & Stutz, E. Streptomycin-resistance of *Euglena gracilis chloroplasts:* identification of a point mutation in the 16S rRNA gene in an invariant position. *Nucleic Acids Res* 13, 4299–310 (1985).

41. Leclerc, D., Melancon, P. & Brakier-Gingras, L. Mutations in the 915 region of *Escherichia coli* 16S ribosomal RNA reduce the binding of streptomycin to the ribosome. *Nucleic Acids Res* 19, 3973–7 (1991).
42. Melancon, P., Boileau, G. & Brakier-Gingras, L. Cross-linking of streptomycin to the 30S subunit of *Escherichia coli* with phenyldiglyoxal. *Biochemistry* 23, 6697–703 (1984).
43. Powers, T. & Noller, H. F. A functional pseudoknot in 16S ribosomal RNA. *Embo J* 10, 2203–14 (1991).
44. Donner, D. & Kurland, C. G. Changes in the primary structure of a mutationally altered ribosomal protein S4 of *Escherichia coli*. *Mol Gen Genet* 115, 49–53 (1972).
45. Funatsu, G., Puls, W., Schiltz, E., Reinbolt, J. & Wittmann, H. G. Ribosomal proteins. XXXI. Comparative studies on altered proteins S4 of six *Escherichia coli* revertants from streptomycin dependence. *Mol Gen Genet* 115, 131–9 (1972).
46. Bock, A., Petzet, A. & Piepersberg, W. Ribosomal ambiguity (ram) mutations facilitate diyhydrostreptomycin binding to ribosomes. *FEBS Lett* 104, 317–21 (1979).
47. Chopra, I., Hawkey, P. M. & Hinton, M. (1992) *J Antimicrob Chemother* 29, 245–77.
48. Ross, J. I., Eady, E. A., Cove, J. H. & Cunliffe, W. J. (1998) *Antimicrob Agents Chemother* 42, 1702–5.
49. Geigenmuller, U. & Nierhaus, K. H. (1986) *Eur J Biochem* 161, 723–6.
50. Eustice, D. C. & Wilhelm, J. M. (1984) *Biochemistry* 23, 1462–7.
51. Brown, C. M., McCaughan, K. K. & Tate, W. P. (1993) *Nucleic Acids Res* 21, 2109–15.
52. Kolesnikov, I. V., Protasova, N. Y. & Gudkov, A. T. (1996) *Biochimie* 78, 868–73.
53. Manavathu, E. K., Fernandez, C. L., Cooperman, B. S. & Taylor, D. E. (1990) *Antimicrob Agents Chemother* 34, 71–7.
54. Burdett, V. (1996) *J Bacteriol* 178, 3246–51.
55. Oehler, R., Polacek, N., Steiner, G. & Barta, A. (1997) *Nucleic Acids Res* 25, 1219–24.
56. Bhuyan, B. K., Dietz, A. & Smith, C. G. (1961) *Antimicrob Agents Chemother*, 184–90.
57. Woodcock, J., Moazed, D., Cannon, M., Davies, J. & Noller, H. F. (1991) *Embo J* 10, 3099–103.
58. Egebjerg, J. & Garrett, R. A. (1991) *Biochimie* 73, 1145–9.
59. Tejedor, F., Amils, R. & Ballesta, J. P. (1985) *Biochemistry* 24, 3667–72.
60. Cohen, L. B., Goldberg, I. H. & Herner, A. E. (1969) *Biochemistry* 8, 1327–35.
61. Carter, A. P., Clemons Jr, W. M., Brodersen, D. E., Morgan-Warren, R. J., Wimberly, B. T. & Ramakrishnan, V. (2000) *Nature* 407, 340–8.
62. Mann, R. L. & Bromer, W. W. (1958) *J. Am. Chem. Soc.* 80,2714–6.
63. Gonzales, A., Jimenez, A., Vasquez, D., Davies, J. E. & Schindler, D. (1978) *Biochim Biophys Acta* 521, 459–69.
64. Cabanas, M. J., Vazquez, D. & Modolell, J. (1978) *Biochem Biophys Res Commun* 83, 991–7.
65. Eustice, D. C. & Wilhelm, J. M. (1984) *Antimicrob Agents Chemother* 26, 53–60.
66. Zierhut, G., Piepersberg, W. & Bock, A. (1979) *Eur J Biochem* 98, 577–83.
67. Spangler, E. A. & Blackburn, E. H. (1985) *J Biol Chem* 260, 6334–40.
68. Moazed, D. & Noller, H. F. (1990) *J Mol Biol* 211, 135–45.

The invention claimed is:

1. A method of identifying a binding partner of the 30S ribosomal subunit comprising the steps of:
    (a) characterizing (i) an active site of the 30S ribosomal subunit from *Thermus thermophilus* from the atomic coordinates found in Table 1A, Table 1B, Table 1C, Table 2, Table 3, or Table 4 or (ii) an active site of a 30S ribosomal subunit by comparison to the atomic coordinates found in Table 1A, Table 1B, Table 1C, Table 2, Table 3, or Table 4, wherein said active site (i) or (ii) is bound by an antibiotic selected from the group consisting of paromomycin, streptomycin, spectinomycin, tetracycline, pactamycin, and hygromycin B and wherein the atomic coordinates of the selected antibiotic appear in the utilized table;
    (b) designing or selecting a binding partner that interacts with said active site (i) or (ii) in the absence of said selected antibiotic; and
    (c) obtaining or synthesizing said binding partner.

2. The method of claim 1, wherein said active site is characterized from the three-dimensional structure of the 30S subunit from the atomic coordinates.

3. The method of claim 1, wherein said active site is characterized from the three-dimensional structure of at least one sub-domain of the 30S subunit from the atomic coordinates.

4. The method of claim 1, wherein said binding partner is an inhibitor of a 30S subunit.

5. The method of claim 1 wherein said active site of step (a)(ii) is characterized by homology modeling using the atomic coordinate data.

6. The method of claim 1 wherein said active site is characterized by molecular replacement using the atomic coordinate data.

7. The method of claim 1 wherein said antibiotic is paromomycin.

8. The method of claim 1 wherein said antibiotic is streptomycin.

9. The method of claim 1 wherein said antibiotic is spectinomycin.

10. The method of claim 1 wherein said antibiotic is tetracycline.

11. The method of claim 1 wherein said antibiotic is pactamycin.

12. The method of claim 1 wherein said antibiotic is hygromycin B.

* * * * *